(12) United States Patent
Rodd et al.

(10) Patent No.: US 8,034,024 B2
(45) Date of Patent: Oct. 11, 2011

(54) NEEDLE CONTAINING MEDICAL DEVICE WITH VARIABLE LOCKING TO NEEDLE HOLDER

(75) Inventors: Aaron Leonard Rodd, Main Beach (AU); Ross Joseph Cali, Main Beach (AU)

(73) Assignee: Medigard Limited (AU)

( * ) Notice: Subject to any disclaimer, the term of this patent is extended or adjusted under 35 U.S.C. 154(b) by 158 days.

(21) Appl. No.: 12/293,024

(22) PCT Filed: Mar. 9, 2007

(86) PCT No.: PCT/AU2007/000299
§ 371 (c)(1),
(2), (4) Date: Feb. 20, 2009

(87) PCT Pub. No.: WO2007/104091
PCT Pub. Date: Sep. 20, 2007

(65) Prior Publication Data
US 2009/0312704 A1 Dec. 17, 2009

(30) Foreign Application Priority Data

Mar. 13, 2006 (AU) ............... 2006901267
Oct. 31, 2006 (AU) ............... 2006906048

(51) Int. Cl.
*A61M 5/00* (2006.01)
(52) U.S. Cl. .................. 604/110; 604/194
(58) Field of Classification Search .......... 604/110, 604/111, 228, 218, 195, 197, 194, 198
See application file for complete search history.

(56) References Cited

U.S. PATENT DOCUMENTS

| | | | |
|---|---|---|---|
| 5,188,599 A | 2/1993 | Botich et al. | |
| 5,389,076 A | 2/1995 | Shaw | |
| 5,462,531 A * | 10/1995 | Novacek et al. | 604/110 |
| 5,520,649 A | 5/1996 | Novacek et al. | |
| 5,658,257 A | 8/1997 | Ryles | |
| 5,820,605 A | 10/1998 | Zdeb et al. | |
| 5,891,104 A | 4/1999 | Shonfeld et al. | |
| 6,066,115 A | 5/2000 | Chang Lai | |
| 6,413,236 B1 | 7/2002 | Van Dyke | |
| 6,599,270 B1 * | 7/2003 | Chen | 604/110 |

(Continued)

FOREIGN PATENT DOCUMENTS
FR 2700959 8/1994
(Continued)

OTHER PUBLICATIONS
International Search Report PCT/AU2007/000299; Dated Jun. 26, 2007.

*Primary Examiner* — Christopher D Koharski
(74) *Attorney, Agent, or Firm* — Cantor Colburn LLP

(57) ABSTRACT

A needle containing medical device having a retractable needle [90], the device comprising an outer body [93], an inner member [97] which can slide within the outer body, a releasable needle holder [91] in a front portion of the outer body, a needle attached to the needle holder, the inner member being provided with a series of spaced needle holder engaging means [108], and the needle holder being provided with a series of spaced inner member engaging means [108] thereby enabling the inner member to be attached to the needle holder at at least one of the series of engaging means.

12 Claims, 17 Drawing Sheets

U.S. PATENT DOCUMENTS

| | | |
|---|---|---|
| 7,381,199 B2 * | 6/2008 | Kuan .............................. 604/110 |
| 7,572,247 B2 | 8/2009 | Smith et al. |
| 2002/0055719 A1 | 5/2002 | Lo |
| 2002/0173750 A1 | 11/2002 | Huang et al. |
| 2002/0177819 A1 * | 11/2002 | Barker et al. ................. 604/232 |
| 2004/0210198 A1 | 10/2004 | Shih |
| 2004/0225263 A1 | 11/2004 | Chen |
| 2005/0080380 A1 | 4/2005 | Hsieh et al. |
| 2005/0203458 A1 | 9/2005 | Shih |
| 2006/0253074 A1 | 11/2006 | Thayer |
| 2006/0264840 A1 | 11/2006 | Thayer |
| 2007/0255212 A1 | 11/2007 | Smith et al. |
| 2007/0260180 A1 | 11/2007 | Smith et al. |
| 2008/0027381 A1 | 1/2008 | Smith et al. |
| 2008/0097306 A1 | 4/2008 | Smith et al. |
| 2008/0114307 A1 | 5/2008 | Smith et al. |

FOREIGN PATENT DOCUMENTS

| | | |
|---|---|---|
| WO | 9307923 | 4/1993 |
| WO | 9711728 | 4/1997 |
| WO | 9819723 | 5/1998 |
| WO | 2004052432 | 6/2004 |
| WO | 2004096326 | 11/2004 |
| WO | 2005089831 | 9/2005 |

* cited by examiner

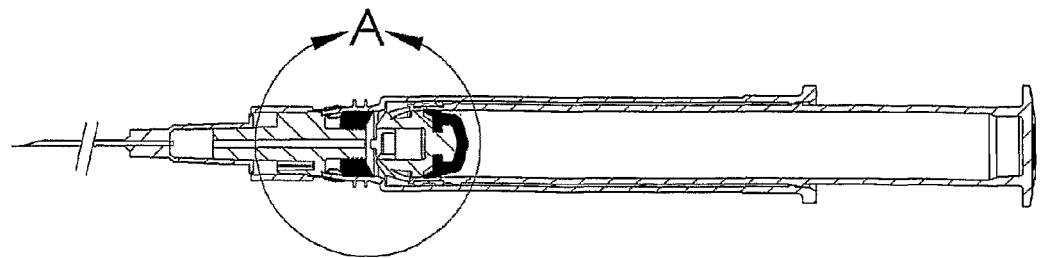
FIG 30
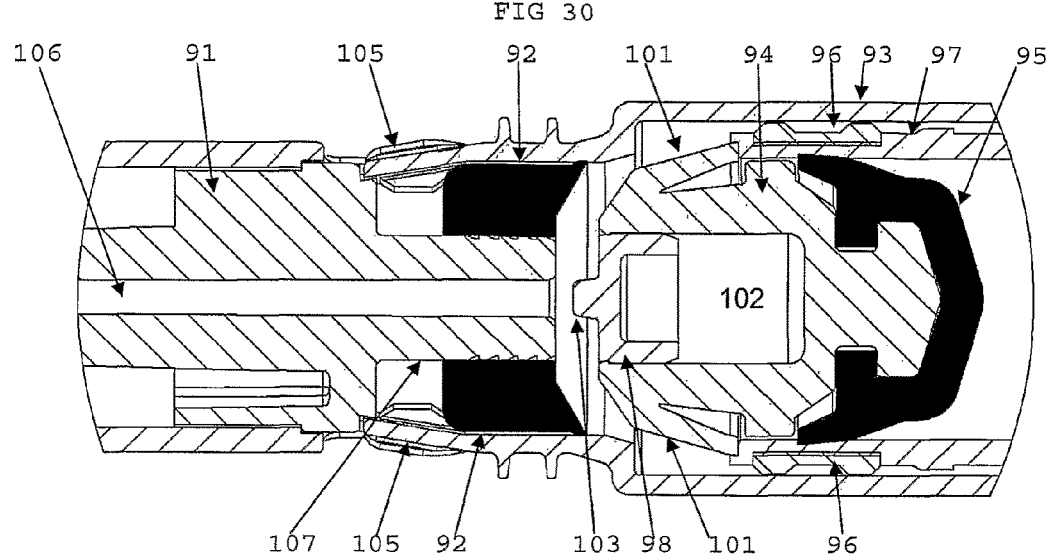
FIG 31
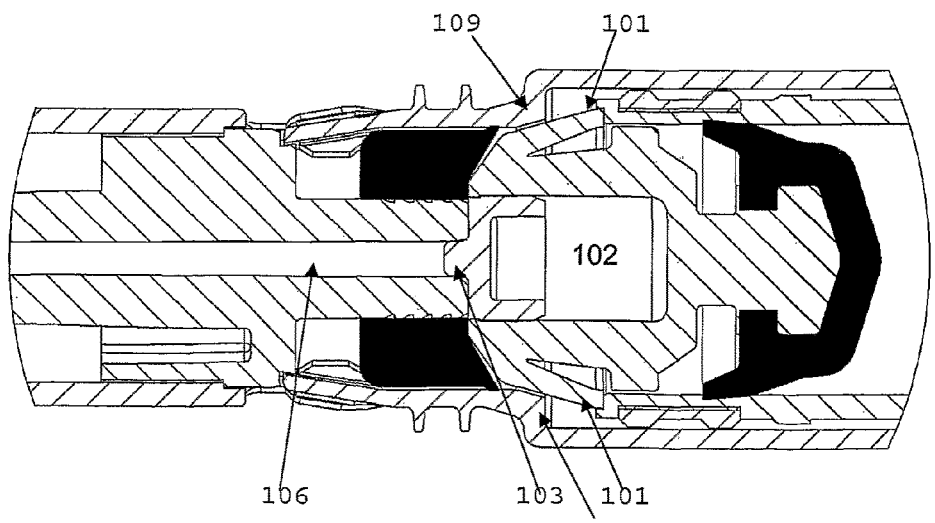

NEEDLE CONTAINING MEDICAL DEVICE WITH VARIABLE LOCKING TO NEEDLE HOLDER

FIELD OF THE INVENTION

The present invention is directed to a medical device of the type having a retractable needle and therefore may include a single use syringe and where improvements have been made to the method by which the needle holder is attached relative to the front of the plunger and the mechanism by which the needle holder is released from the front of the syringe. The present invention may also be directed to other improvements to such devices.

BACKGROUND ART

With the ever-increasing awareness of needlestick injury and the risks associated with sharing needles, there have been many syringes introduced in the marketplace having some form of retractable needle. There are three basic types.

The first type can be seen as a "manual"-type syringe where, as the plunger is moved forwardly towards the end of the syringe barrel, it couples with a needle holder which contains the needle. The plunger can then be manually retracted which causes the needle to be retracted into the syringe body.

The second type can broadly be classified as "shoot back" syringes. In these syringes, some form of spring is provided. As the plunger is pushed forwardly towards the end of the syringe barrel, the needle holder is released and the spring causes the needle holder (containing the attached needle) to shoot back, either into the plunger body or into the syringe body. The spring may be mounted about the needle holder and under permanent compression until the needle holder is released. Alternatively, it is known to provide a spring that stretches as the plunger is pushed forwardly towards the front of the syringe barrel.

The third type can be broadly classified as "suck back" syringes. In these syringes, a reduced pressure (vacuum) is typically provided in the plunger and the front of the plunger is sealed by a piston. The piston is releasably mounted to the front of the plunger. The front of the syringe barrel has a releasable needle holder which contains the needle. As the plunger is pushed forwardly towards the end of the syringe barrel, the piston couples to the needle holder and at the same time, the piston is released from the front of the plunger and the needle holder is released from the front of the syringe barrel which causes the needle holder/piston to be sucked back into the plunger by the vacuum.

There are many variations to these three basic constructions. For instance, it is known to provide a "vacuum on demand" to the plunger which means that the syringe can be at atmospheric pressure until just before use at which stage a vacuum can be created in the plunger.

In each of the basic constructions, great care needs to be taken that the plunger (which may include a piston) properly couples to the needle holder such that the needle holder (containing the contaminated needle) can be properly retracted.

With a manual retraction, it is undesirable that a situation can occur where retraction of the plunger does not cause retraction of the needle holder.

With a shoot back mechanism, it is highly undesirable that the mechanism "triggers" either too soon or too late. If the mechanism triggers too soon, there may still be appreciable medicine in the syringe which will be lost if the needle shoots back prematurely. Alternatively, it is also highly undesirable if the mechanism does not trigger when the plunger is pushed fully forwardly, or where it is necessary to place undue force on the plunger (which can damage the shoot back mechanism).

With a "suck back" mechanism, it is also highly undesirable that the mechanism triggers too soon or too late. With this type of mechanism, because the plunger is under vacuum, if the piston on the front of the plunger releases too early, the piston can be retracted (sucked back) into the plunger body without properly attaching to the needle holder. Alternatively, it is equally undesirable that the needle holder is released too early.

However, it is found that the particular construction of the single use syringes is such that there is not much "leeway" in the triggering mechanism, and particularly if the syringes are the small 1 ml syringes. Thus, the possibility of the release mechanism triggering either too late or too soon is ever present.

One cause for the premature triggering of the release mechanism seems to be that the plunger needs to engage with the retraction device almost immediately upon the plunger being pushed into a forward part of the syringe. Thus, if the engagement does not occur immediately, there may be malfunctioning of the release mechanism.

Another possible cause for premature triggering or delayed triggering may be in the way that the needle holder (often also called a luer) is attached in a releasable manner to the front of the barrel. It is known to hold the needle holder in a releasable manner to the front of the barrel using some sort of functional engagement, and when the plunger is pushed towards the front of the barrel, the plunger engages in some manner with the needle holder to reduce to frictional engagement to such an extent that the needle holder can now be triggered to the retracted position. It is found that a frictional engagement of the needle holder to the barrel is not necessarily an entirely satisfactory arrangement.

Therefore, it is also known to provide some form of step or shoulder in the front of the barrel against which the needle holder can be held and it is then necessary to push the step or shoulder away to release the needle holder. It is also known to provide some form of "shatter plate" which is broken to release the needle holder, or some form of frangible portion. While some of these arrangements can provide a satisfactory temporary attachment of the needle holder in place, the manufacture of the step or shoulder in the front of the barrel can be quite difficult.

It would therefore be an advantage to modify the particular construction of single use syringes, including of the "suck back" type to improve the design by which the piston can be released from the front of the plunger and/or the design by which the needle holder can be released from the front of the syringe barrel.

It will be clearly understood that, if a prior art publication is referred to herein, this reference does not constitute an admission that the publication forms part of the common general knowledge in the art in Australia or in any other country.

OBJECT OF THE INVENTION

It is an object of the invention to provide a needle containing medical device with a retractable needle which can overcome at least some of the above-mentioned disadvantages or provide a useful or commercial choice.

In a first broad form, the invention resides in a needle containing medical device having a retractable needle, the device comprising an outer body, an inner member which can slide within the outer body, a releasable needle holder in a front portion of the outer body, a needle attached to the needle holder, the inner member being provided with a series of spaced needle holder engaging means, and the needle holder being provided with a series of spaced inner member engaging means thereby enabling the inner member to be attached to the needle holder at least one of the series of engaging means.

This provides a degree of "leeway" or "adjustability" by enabling the inner member to become connected to the needle holder over a particular distance as opposed to just one point. Thus, the inner member can become attached to the needle holder at the first engaging means, and should the retraction mechanism trigger, the needle holder will be attached and retracted. However, if the retraction mechanism has not yet triggered, the inner member can be pushed further forward to engage against another engaging means (or possibly multiple engaging means) and if the retraction mechanism then triggers, the needle holder will still be retracted.

In a more particular form, the invention resides in a needle containing medical device having a retractable needle, the device comprising an outer body, an inner member which can slide within the outer body, a needle holder (sometimes called a luer) in a front portion of the outer body, a needle attached to the needle holder, at least one zone in the outer body which can move between a locking position where the needle holder is locked to the outer body, and a free position where the needle holder can be retracted into the body, the inner member having a front portion containing a piston, the front portion or the piston being provided with a series of spaced needle holder engaging means, and the needle holder being provided with a series of spaced front portion or piston engaging means thereby enabling the inner member to be attached to the needle holder at least one of the series of engaging means.

If the medical device comprises a single use syringe, the outer body can comprise the syringe barrel, and the inner member can comprise the plunger.

If the medical device comprises a single use syringe, it is preferred that the single use syringe contains the at least one zone in the outer body to hold the needle holder in position.

This overcomes a potential disadvantage with various other needle holding mechanisms which are more complicated and which may not be as reliable as they should be.

By having a zone in the outer body (e.g. the syringe barrel) and having this zone able to be flexed between the locking position and the free position, there is provided a simple yet robust and reliable way to hold the needle holder in position.

The zone can be flexed from the locking (needle holding) position to the free (release) position by forward movement of the inner member (e.g. the plunger). For instance, as the inner member pushes forwardly into the outer body, it can cause the at least one zone to be flexed from the locking position to the free position to release the needle holder.

It is preferred that the outer body contains more than one zone but it is not preferred that the zone is continuous about the outer body as this can provide disadvantages including unnecessary weakening of the outer body and requiring excessive force to push the inner member (piston) past of this continuous zone.

Therefore, the outer body can comprise between 2-6 and preferably 4 such zones and these can be equally spaced about the outer body such that the area between the zones can be made "full thickness" to provide strength to this part of the outer body.

The zones themselves may comprise some form of profile or shoulder or projection (hereinafter called "profile") against which the needle holder can be held and surrounded by an at least partially flexible portion such that the profile can be flexed from the locking to the released position when required. In a simple embodiment, the at least partially flexible portion may comprise a thinner wall section around the profile and which is attached to the remainder of the outer body such that the outer body remains continuous and does not contain any openings (such as slots, slips and the like). Of course, it is considered that other types of construction can be used to provide a zone. For instance, the at least partially flexible portion may comprise a plurality of "thin wall" ribs or portions that can allow the profile to flex away and where the area between these portions contains a "full thickness" wall portion or something else. It is also envisaged that some form of elastic property may be provided to allow the zone to be stretched from the locking to the free position.

The needle holder can be directly or indirectly held by the, or each, zone or at least some of the zones. For ease of construction, it is preferred that the needle holder abuts directly against the profile of the zone.

The medical device contains a particular construction to allow the inner member to be attached to the needle holder along at least one of a plurality of spaced apart positions (engaging means) to provide some leeway or adjustability.

The engaging means may comprise a series of spaced apart raised portions. These portions may comprise ribs, walls, flanges, teeth, hooks, buttons, a combination of these, and the like. Alternatively, the engaging means may comprise a series of spaced apart recesses. These recesses may comprise grooves, slits, slots, holes, dimples, a combination of these and the like. A combination of recesses and raised portions may be provided.

The recesses and the raised portions may be continuous or discontinuous.

The engaging means will typically be such that the inner member can be connected to the needle holder along a spacing of between 1-20 mm and typically between 1-10 mm. Thus, the length or width of the engaging means will be commensurate with this.

In a simple embodiment, the engaging means may comprise a series of circumferential spaced apart ribs on the inner member and a series of circumferential spaced apart ribs on the needle holder, the construction and arrangement being that the ribs can engage to lock the inner member to the needle holder.

The outer body may comprise a syringe barrel or something similar depending on the particular use of the medical device. The length and diameter (or cross-section) of the barrel can vary depending on use. It is envisaged that the outer body will have a length of between 30 or 50 mm (for the small single use syringes—typically 1 ml), up to 100-200 mm for the larger syringes. Similarly, the diameter (or cross-section if the outer body is not circular) can be between 3-50 mm.

The outer body and inner member will typically be made of plastic, plastic composites, glass and the like.

The inner member will typically comprise a plunger or something similar depending on the particular use of the medical device. The inner member will have a forward portion (which is the portion which moves closest towards the front of the syringe barrel) and a rear portion (which typically extends from the rear of the syringe barrel). If the inner member is a plunger, it may have all the usual plunger design features such as a thumb plate on the rear portion and the like.

The forward part of the plunger will typically contain a separate part which can be called a piston. Alternatively, the forward part of the plunger may be profiled to contain a part which can be called a piston. Unless the context provides otherwise, it is not considered that the term "piston" should be construed unnecessarily narrowly. Throughout the specification and claims, the term "piston" is meant to include a forward part or profile on the inner member (e.g. plunger) which can connect to the needle holder and which may be retracted either manually or automatically.

It is preferred that the piston contains the engagement means such that the piston can be attached to the needle holder.

The piston may be releasably attached to the front of the plunger such that it can be "sucked back" into the plunger body to retract the needle holder and the contaminated needle.

Alternatively, the piston may form part of the front of the plunger and is not releasably attached to the front of the plunger and it is necessary to retract the entire plunger to retract the needle holder and the contaminated needle (this being called the manual version of the invention).

The piston may have a portion which can cause the at least one zone to flex to the release position as the piston is pushed forwardly into the outer body (e.g. syringe barrel). This portion may comprise a shoulder, abutment, or any other type of profile or means that can function in this manner. Alternatively, the piston may support a separate member either directly or indirectly which can cause the at least one zone to flex. However, for ease of manufacture, it is preferred that the piston itself abuts against and flexes away the at least one zone.

In a preferred embodiment, the portion may comprise a circumferential abutment or shoulder such that the portion will flex away all the zones that may be present on the outer body. In this way, it is not necessary to align the portions with the zones, as by having the portion as a circumferential abutment or shoulder, it will always flex the zones away irrespective of the exact rotational position of the piston in the outer body.

Another requirement for syringes is that all the medication is ejected from the syringe when the plunger is pushed fully forwardly. That is, it is undesirable to have any "dead spaces" in the syringe which contain medication which cannot be ejected through the needle. With conventional syringe designs, the front of the plunger is relatively planar and virtually all the medication can be pushed through the needle. However, many needle retraction mechanisms require a particular profile either on the front of the plunger or the needle holder and in many cases this gives dead space in the syringe which is not desirable.

Therefore, another improvement in the present invention is to provide the needle holder with a recess which communicates with the needle and to provide the front of the inner member (e.g. the piston) with a nose portion that can pass into the recess to minimise any dead space in the syringe.

One version of the present invention has a releasable piston on the front of the plunger and the plunger can be placed under vacuum such that when the piston is released (and coupled to the needle holder), it is retracted into the plunger body under the influence of vacuum.

In this version of the invention, the piston may have releasable engagement means to releasably engage it to a forward portion of the inner member (typically plunger). The engagement means may comprise at least one and preferably a plurality of finger members that engage with a forward portion of the inner member to lock the piston in place, but which can be moved to a release position to release the piston from the front of the inner member. These finger members may be cantilevered and can be depressed to the release position. Alternatively, other release means may be provided such as some form of rotation of release means and the like. It is preferred that the releasable engagement means moves to the release position when the inner member is pushed to the front of the outer body and it is preferred that the releasable engagement means moves to the release position by abutment against some part of the outer body.

In second broad form, the invention resides in a needle containing a medical device having a retractable needle, the device comprising:

an outer body (e.g. a barrel) having a front portion through which the needle can extend, and a rear portion, an inner member (e.g. a plunger) which can slide within the outer body, a releasable needle holder (for instance, a luer) in a front portion of the outer body, a needle attached to the needle holder, wherein the front portion of the outer body contains at least one side opening extending therethrough, a clip having one part attached relative to the outer body, and extending in a cantilevered manner at least partially along the side opening, the clip naturally being in a needle holding position but able to be deflected to a needle release position, and wherein the inner member is able to move within the outer body to the front portion of the outer body and wherein the inner member is able to deflect the at least one clip to the release position thereby enabling the needle holder to be retracted.

It is preferred that the needle containing medical device of the second broad form of the invention also contains the variable locking previously described. Alternatively, it is preferred that the needle containing medical device of the first broad form of the invention contains the at least one clip and other features described in the second broad form of the invention.

An advantage of this particular needle holding arrangement is that the needle holder can be quite positively and firmly held by the at least one clip (usually two or more clips will be provided spaced about the side wall of the outer body and adjacent the front portion of the outer body). Thus, the needle holder is not held in the front of the outer body (e.g. barrel) only by friction or by a shatter ring and the like. Another advantage of this particular arrangement is that it may be easier to manufacture the front of the barrel with the at least one clip if the area about the clip can be "punched out" or otherwise removed such that the clip comprises a "spring finger" or similar cantilevered member extending along the opening. Another advantage is that by having the clip cantilevered and thereby relatively free (apart from where the clip is attached to the side wall of the barrel), the clip can be reliably moved from the needle holding position to the pushed away/deflected etc. needle holder release position. Generally, it is found that this particular type of arrangement to releasably lock the needle holder to the front of the barrel (e.g. with the at least one clip) is superior to the use of friction only.

In this second broad form of the invention, because it is preferred that openings are provided in the side wall of the outer portion (e.g. the barrel), it is envisaged that some redesign of the needle holder or other parts may be necessary to prevent medicine in the barrel from passing through the opening in the side wall as opposed to through the needle.

The outer body may comprise a syringe barrel and may have at least some of the features described previously above. The outer body contains at least one side opening to accommodate a clip to releasably hold the needle holder (which can also be called the luer). It is envisaged that more than one side opening will be provided and, for a typical syringe, it is envisaged that a pair of side openings will be provided on opposite sides of the syringe barrel.

The shape and size of the side opening may vary, depending at least on the size of the barrel. It is envisaged that the shape of each opening will be somewhat rectangular. It is also envisaged that the length of each opening will typically be between 2-10 mm and a width of each opening will typically be between 2-5 mm but this may vary depending on the size of the syringe.

It is envisaged that the, or each, side opening will be in the front portion of the barrel or other outer part of the device. It is envisaged that the side opening will be spaced inwards from the front end of the front portion by a distance which is sufficient to allow at least part of the needle holder to be positioned in front of the side opening (and therefore able to be releasably attached by the clips), while still enabling part of the needle holder to be positioned within the confines of the front portion. Therefore, it is envisaged that the, or each, side opening will be spaced inwardly by a distance of between 10-50 mm from the front end of the outer part.

The clip will typically be of a size and shape to enable it to be positioned in the side opening. It is envisaged that the clip will be made of the same material as the outer body. The clip will typically be "cantilevered" from one edge of the opening and typically in such a manner that the free end of the clip extends towards the front of the barrel. By being cantilevered, the clip will have a degree of "spring" which is desirable to enable it to releasably hold the needle holder (luer).

The shape of the clip can vary but it is considered desirable that the portion of the clip that releasably engages to the needle holder is shaped in such a manner that a good connection between the clip and the needle holder can be made.

To provide a degree of "spring" to the clip, it is envisaged that the portion of the clip that is attached to one edge of the opening (this can be called the necked portion) has a reduced thickness.

It is envisaged that the clip will substantially fill the opening such that there is only a small gap between the edge of the clip and the edge of the opening, the gap being sufficient to give the clip free movement between the engaging position and the release position.

Thus, there may be circumstances where the side opening is not rectangular and may have an oval shape, or an irregular shape, and in these circumstances, the clip may have a similar shape.

The inner member may comprise a plunger which may have at least some of the features described previously above. The plunger is preferably under reduced pressure (vacuum), and this can be provided during the manufacturing process or may be provided "upon demand" for instance just prior to use of the device.

The releasable needle holder may contain part of the "variable locking" mechanism described above to enable the releasable holder to lock to the front of the plunger (or other type of inner member).

The needle holder may contain a forwardly extending nose portion, a rear stem portion, and an intermediate side portion. A longitudinal passage will typically extend through the needle holder to accommodate the needle and to provide a passageway for medicine to flow through the needle holder and through the needle.

The intermediate side portion typically contains an abutment or shoulder or something similar to engage against the clip to releasably lock the needle holder in place. Typically, the intermediate side portion will be cylindrical and will therefore contain an annular abutment or shoulder to engage with the, or each, clip.

The stem portion extends rearwardly into the outer portion (e.g. barrel) and typically faces the plunger. It is preferred that the stem portion contains part of the variable locking means described above.

A sealing means will typically be provided behind the at least one clip on the barrel and typically to seal the needle holder thereby preventing medicine from passing through the opening around the at least one clip. The sealing means may be attached to the stem portion of the needle holder. Typically, the sealing means will initially extend about the portion of the stem portion that also contains part of the variable locking means. It is therefore preferred that the sealing means is also able to be pushed forwardly along the stem portion to expose this part of the variable locking means. Thus, the sealing means may comprise an annular ring containing a central opening through which the stem portion of the needle holder can pass, the construction being that the sealing means can be pushed along the stem portion (typically by the plunger). This will be described in greater detail below.

In a particularly preferred embodiment, the sealing means is positioned about the stem portion of the needle holder (luer), and beneath the at least one clip on the barrel.

The sealing means may be made of any suitable material such as rubber, plastic, silicone and the like.

The inner member may comprise a plunger. The plunger may be under reduced pressure (vacuum). The plunger may comprise an elongate substantially hollow body having a closed rear end and an open front end, the open front end being sealed by a sealing member that is releasably attached to the open front end. The sealing member may comprise a piston. The piston may be provided with means to releasably attach the piston to the front of the plunger. The means may comprise at least one clip, or at least one finger member, or some other means. The at least one clip may be movable between a locking position where the piston is locked to the otherwise open front end of the plunger, and the release position where the piston can be retracted into the plunger body (by the vacuum in the plunger body). The at least one clip may comprise a cantilevered member which will be described in greater detail below.

The piston may comprise, or include a vacuum seal to enable the piston to sealingly engage to the front of the plunger to prevent loss of vacuum in the plunger body.

The piston may have a forward portion or face which is configured to push the seal on the rear stem portion of the needle holder forwardly as the plunger is pushed towards the front of the barrel. As an example, the forward portion or face may be somewhat tapered or curved.

The forward portion of the piston may contain a recess to accommodate part of the stem portion of the needle holder, and the recess may be provided with the variable locking means described previously thereby enabling the piston to attach to the rear of the needle holder at one or more positions.

It should be appreciated that any reference made to a publication or citation is not imply that the publication or citation forms part of the common general knowledge in Australia or elsewhere.

BRIEF DESCRIPTION OF THE DRAWINGS

Four embodiments of the invention will be described with reference to the following drawings in which.

First Embodiment of the Invention

Second Embodiment of the Invention (Manual Version)

Figure 9:
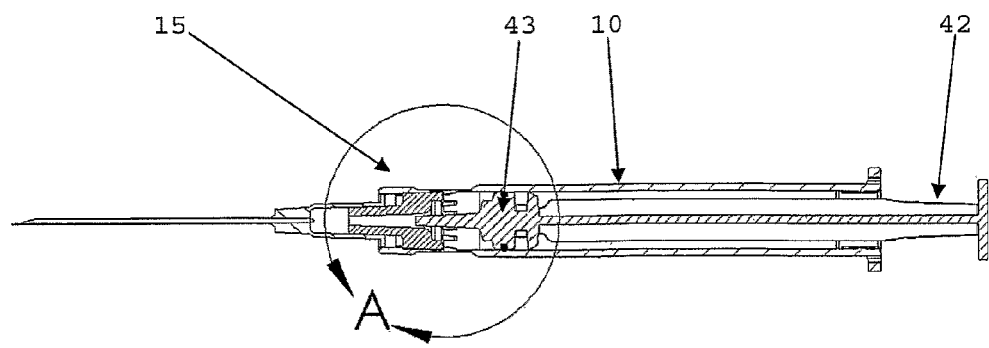

FIG. 9 illustrates a section view of the syringe.

Figure 10:
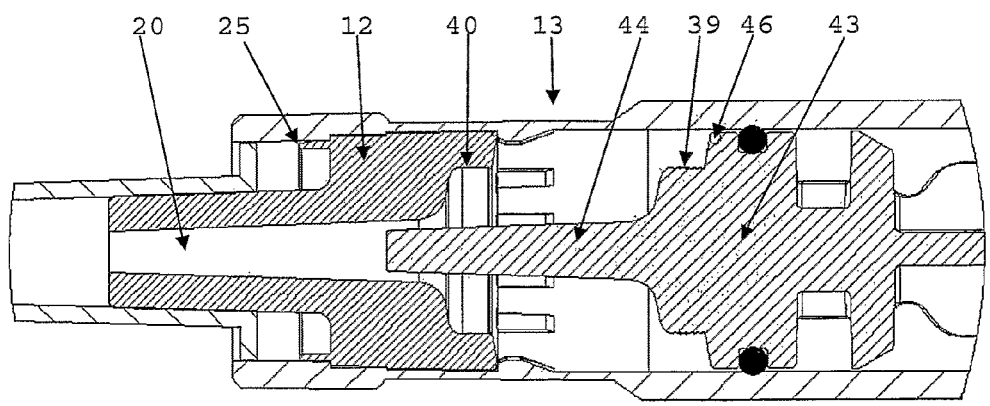

FIG. 10 illustrates the piston in the forward position where the needle holder has not yet been released and the piston has not yet been attached to the needle holder.

Figure 11:
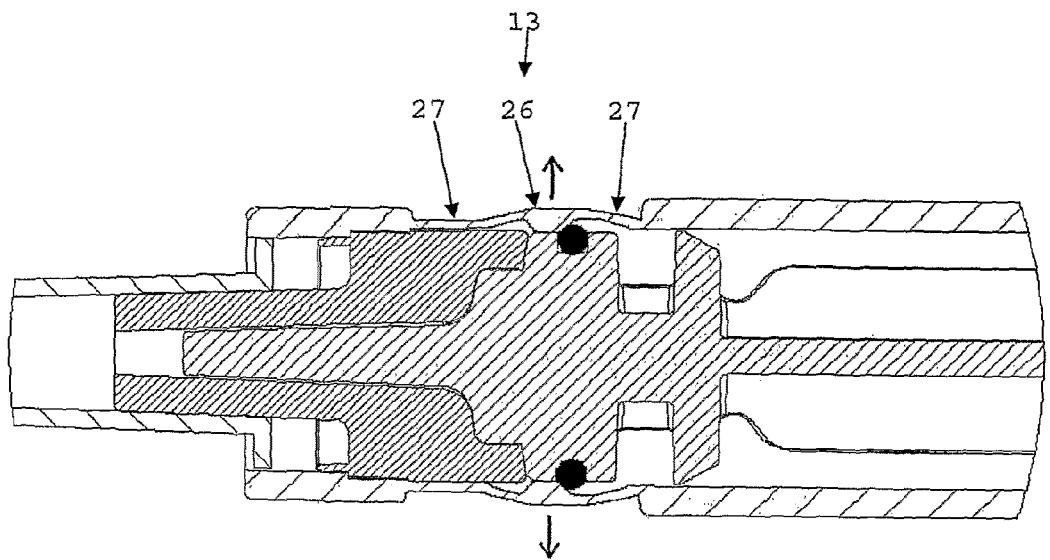

FIG. 11 illustrates the piston having been moved further forwardly and having flexed back the zones in the syringe body to release the needle holder and also having attached itself to the needle holder.

Figure 12:
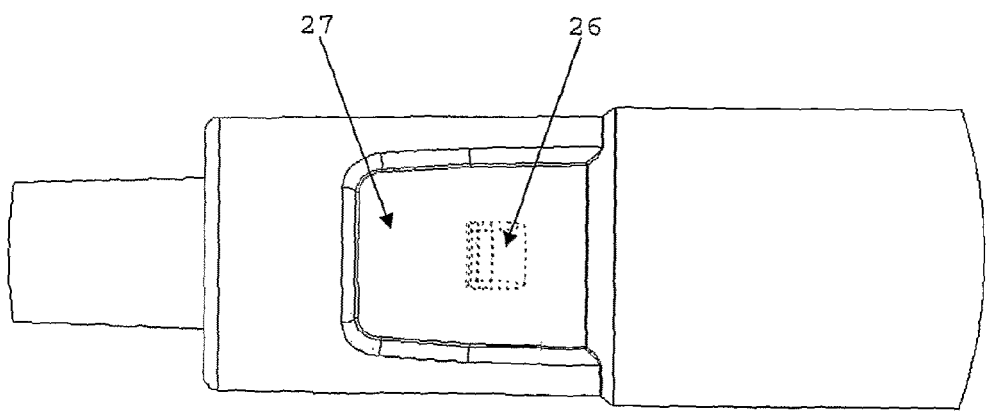

FIG. 12 illustrates one zone on the outside of the syringe body.

Figure 13:
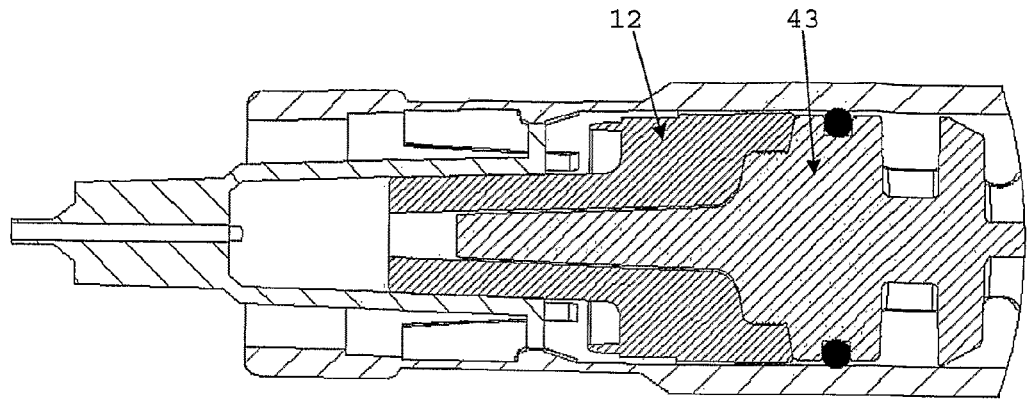

FIG. 13 illustrates the initial retraction of the piston containing the attached needle holder.

Figure 14:
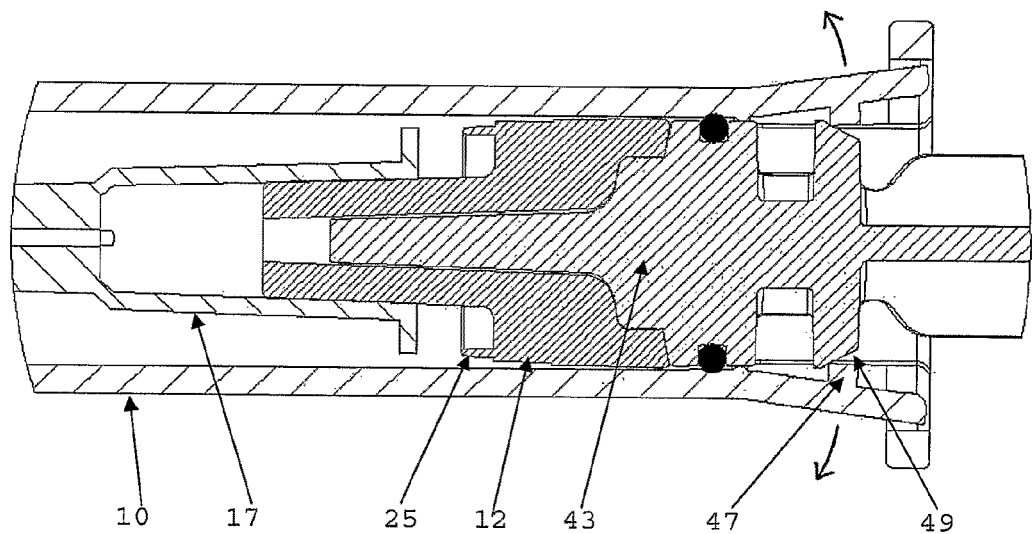

FIG. 14 illustrates full retraction of the piston in the syringe body and about to be locked into the back of the syringe body.

Figure 15:
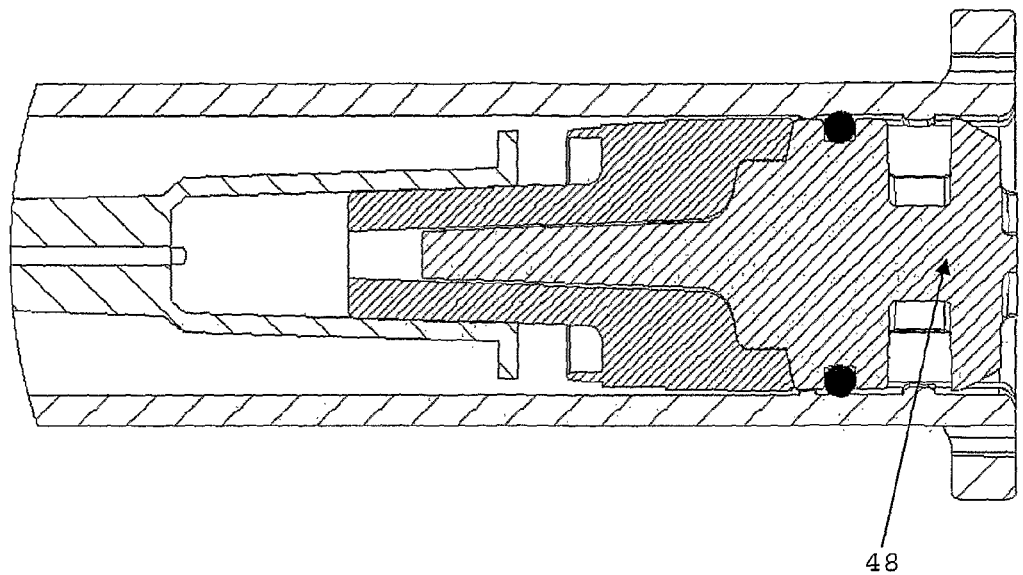

FIG. 15 illustrates the piston locked to the back of the syringe body and therefore unable to be pushed forwardly to re-expose the contaminated needle.

Figure 16:
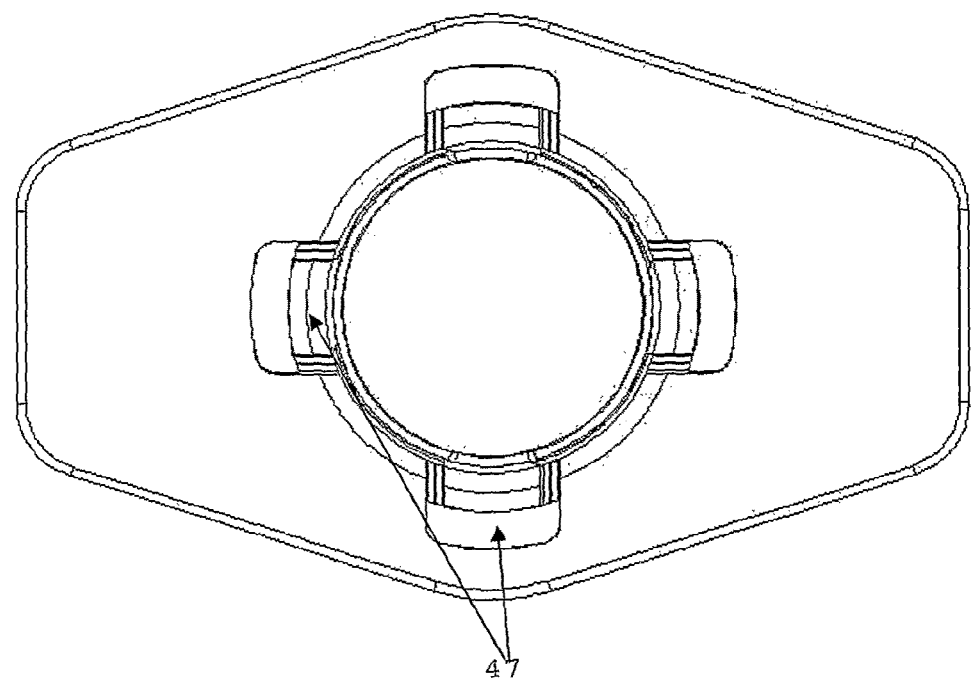

FIG. 16 illustrates a rear view of the syringe and particularly illustrates the four locking lugs to lock the piston to the back of the syringe body.

Figure 17:
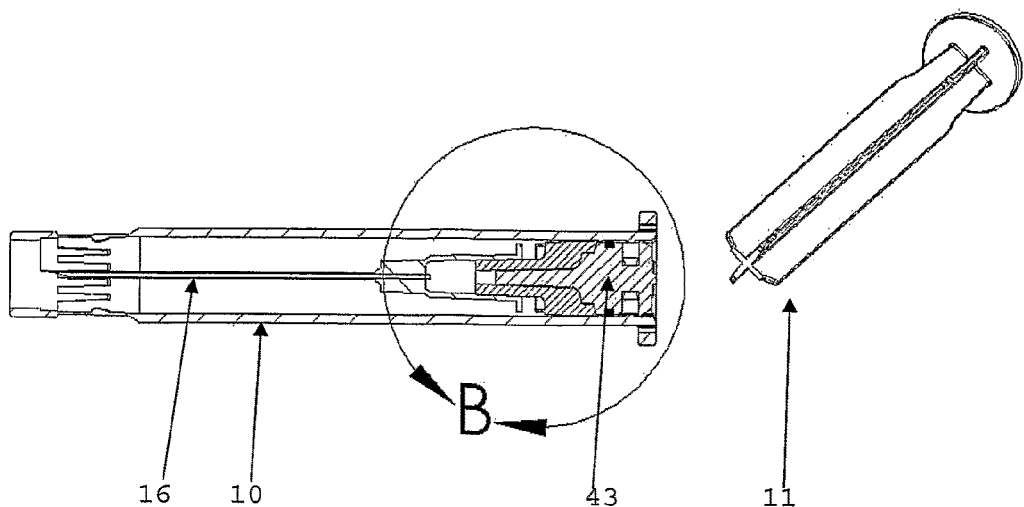
Figure 18:
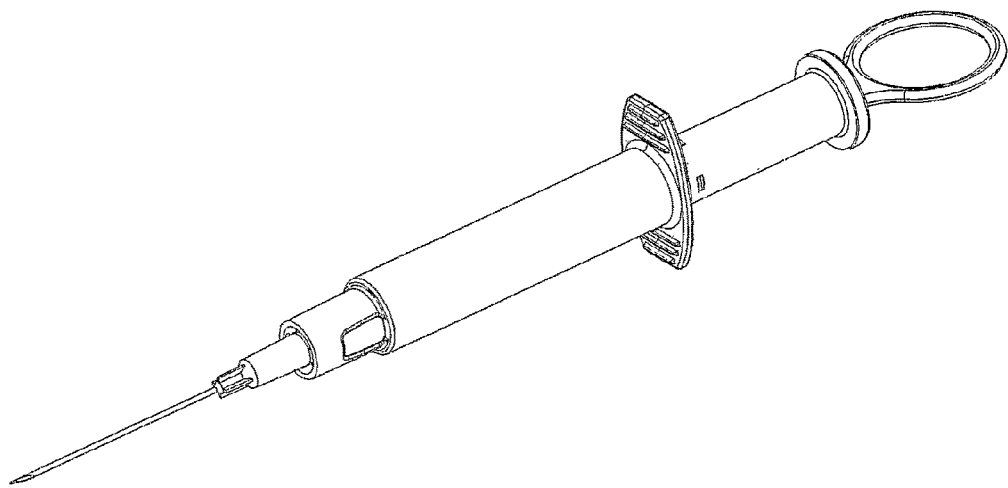
Figure 19:
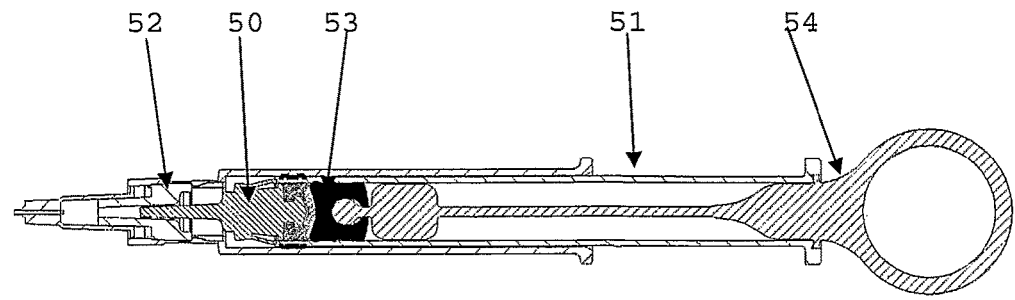
Figure 20:
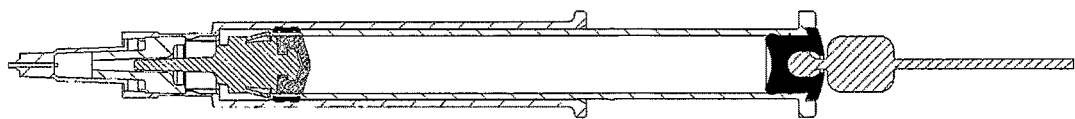

FIG. 17 illustrates how the plunger can be snapped away from the piston.

Third Embodiment of the Invention

FIGS. 18-21 illustrate a third embodiment of the invention where vacuum can be produced upon demand.

Fourth Embodiment of the Invention

FIGS. 22-28 illustrate a fourth embodiment of the invention where cantilevered clips are used to hold the needle holder.

Fifth Embodiment of the Invention

FIGS. 29-35 illustrate a fifth embodiment of the invention.

BEST MODE

First Embodiment of the Invention (FIGS. 1-8)

Referring initially to the first embodiment of the invention, this particular embodiment is directed to a retractable single use syringe, although it should be appreciated that it is not considered that the invention should be limited only to a single use syringe.

In the particular embodiment, there is described a needle containing medical device (a syringe) which has an outer body in the form of a syringe barrel 10, an inner member in the form of a plunger 11, a needle holder 12, a number of separate zones 13 on syringe barrel 10, and a piston 14 attached to the front of plunger 11.

Referring now in greater detail to the particular embodiment, syringe barrel 10 has a typically cylindrical outer shape and has a front portion 15 which contains zones 13. Front portion 15 has a reduced diameter with respect to the remainder of barrel 10. A needle 16 of conventional design is fitted to its associated luer 17.

Figure 2:
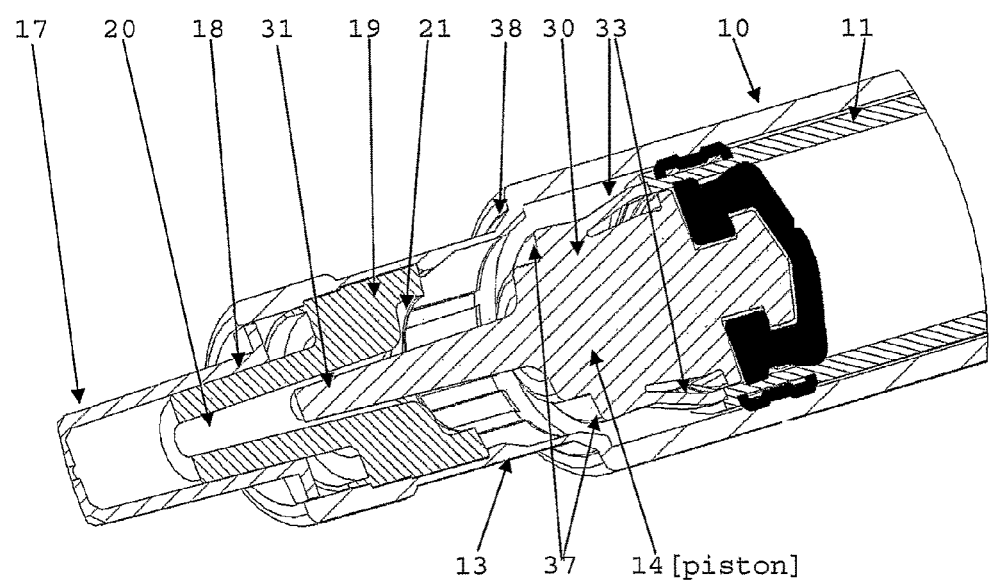
FIG. 2 illustrates a cross-section view showing the needle holder and the piston and where the release mechanism has not yet triggered.

Referring to FIG. 2, inside the front portion 15 of barrel 10 is the needle holder 12. The needle holder 12 has a nose portion 18 and luer 17 can be press fitted over the top of nose portion 18 in the usual manner.

Needle holder 12 is formed of plastics material and is of a unitary design. Specifically, needle holder 12 has a main body portion 19 in front of which is nose portion 18. A rather large passageway 20 extends entirely through needle holder 12. Passageway 20 is much larger in diameter than the diameter of needle 16 and passageway 20 also tapers slightly from a larger rear portion (communicating with barrel 10) to a smaller front portion (communicating with needle 16).

Passageway 20, at the rear end, communicates with a much larger recess 21 formed in the needle holder 12. The rearmost portion of needle holder 12 comprises a flat annular surface 22, which is probably best illustrated in FIG. 7. The flat annular surface 21 is what holds the needle holder in place in the front of barrel 10 and this will be described in greater detail below.

Figure 5:
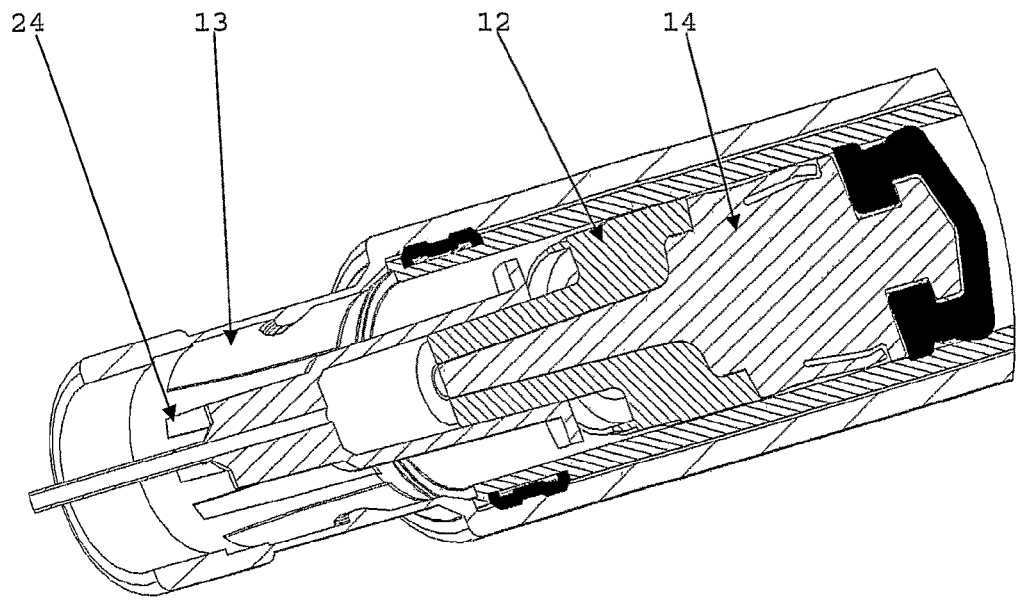
FIG. 5 illustrates the piston containing the attached needle holder being retracted.
Figure 7:
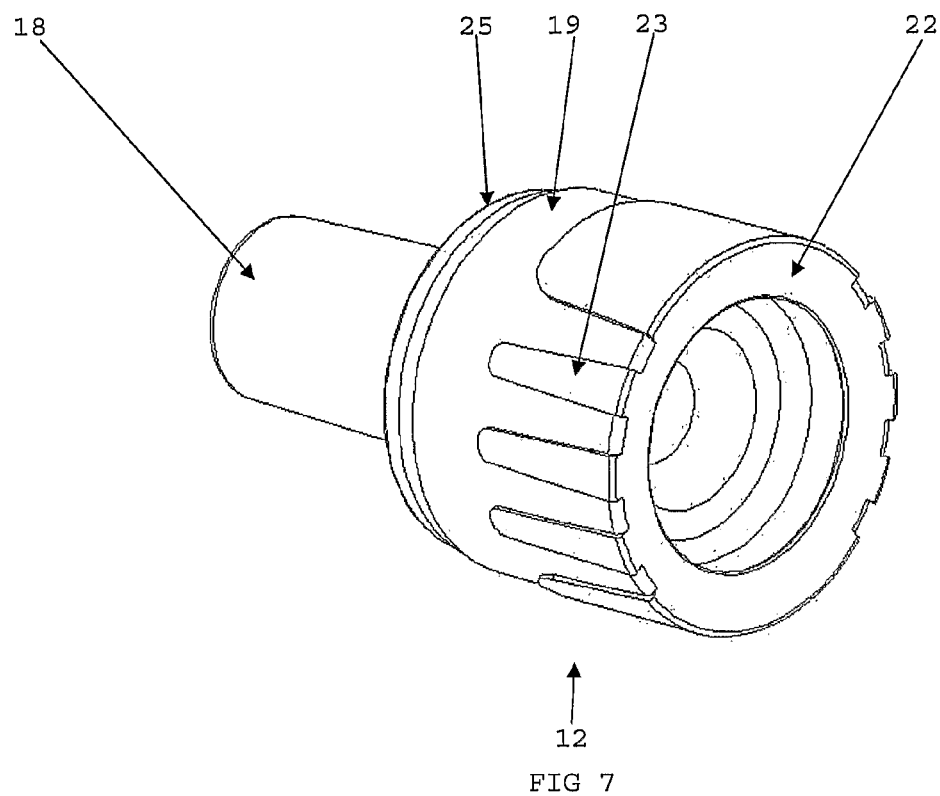
FIG. 7 illustrates the needle holder.

Also best illustrated in FIG. 7 is a plurality of longitudinal anti-rotation splines 23. These engage with corresponding splines 24 formed in the front portion 15 of barrel 10 and splines 24 are best illustrated in FIG. 5. Thus, needle holder 12 can slide forwardly or rearwardly in the barrel but cannot rotate.

Figure 3:
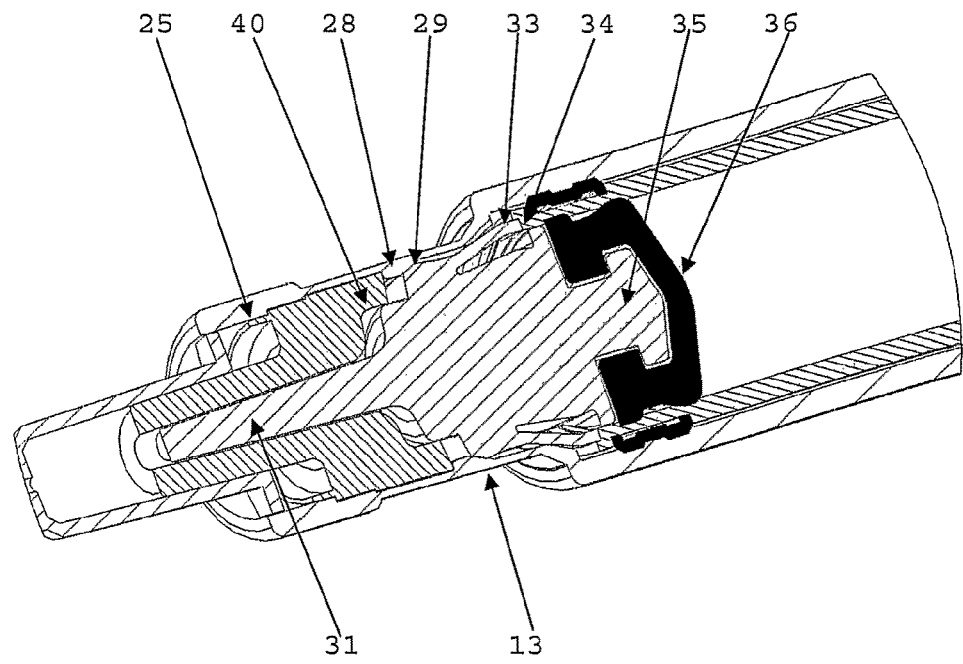
FIG. 3 illustrates the piston having moved further forwardly and beginning to engage with the needle holder and where the release mechanism has not yet been triggered.
Figure 4:
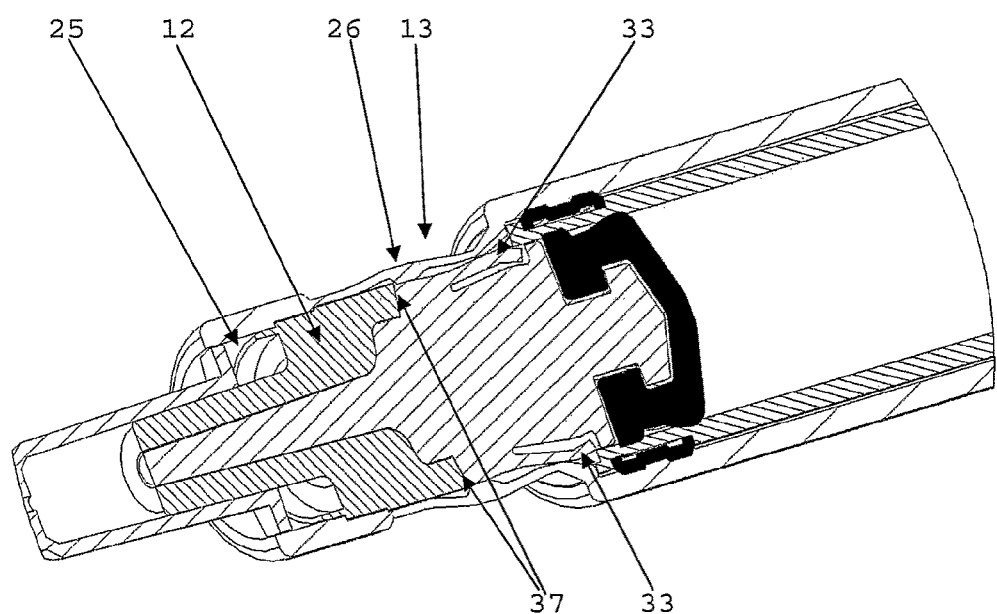
FIG. 4 illustrates the piston having moved further forwardly and where the release mechanism has just been triggered and therefore where the needle holder has been released and the piston has also been released.

Also illustrated in FIG. 7, but also in FIGS. 2-4, is a ring-shaped relatively flexible sealing flange 25 (reference 25 given in FIG. 3, FIG. 10 and FIG. 7) which extends forwardly (that is towards the nose portion 18) and which is biased against the inside wall of front portion 15 of barrel 10. This provides sealing against any fluid passing between the needle holder 12 and the inside wall of front portion 15.

Figure 1:
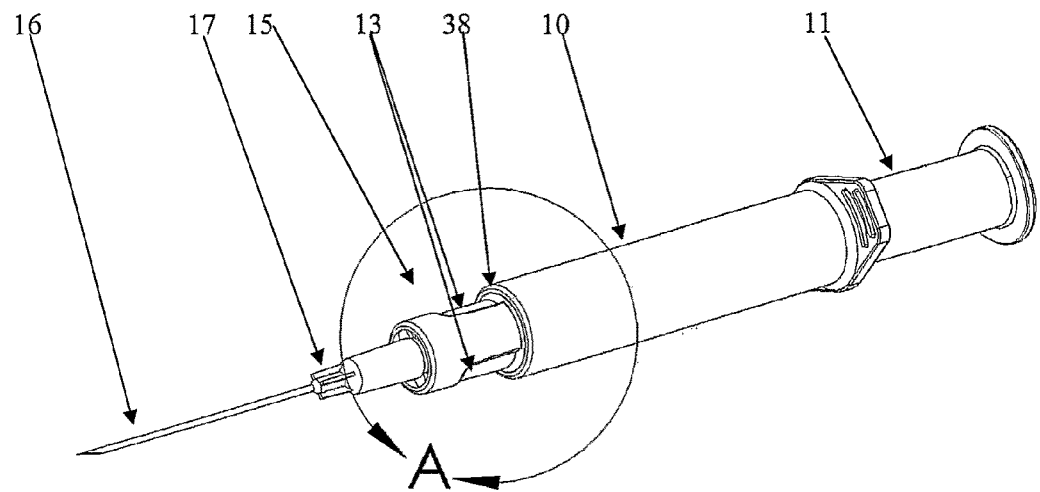
FIG. 1 illustrates generally a single use syringe according to a first embodiment of the invention.

The positioning of needle holder 12 and the "locking" of the needle holder in the front of barrel 10 (and particularly in front portion 15) requires an understanding of the zones 13. The zones 13 are best illustrated in FIG. 1 and FIG. 12. These zones have a particular design and comprise a centralised profile 26 which is probably best illustrated in FIG. 12 and a surrounding somewhat flexible web portion 27. In the first embodiment, there is provided two diametrically opposed zones 13 in front portion 15. Importantly, the zones are continuous in the sense that they do not provide any openings etc. through barrel 10, so there is no possibility of any fluid flowing through the zones. Instead, the zones can be seen as having a relatively centralised hardened profile 26 surrounded by a somewhat flexible web portion 27 and the web portion 27 can be a "thin wall" portion of barrel 10. This is perhaps also best illustrated in FIG. 11 which shows, in section view, profile 26 and the surrounding thin wall web portion 27.

Profile 26 has a shoulder like or other type of projection 28 (see FIG. 3) extending inwardly into the inside of forward portion 15 of barrel 10, and it is against this projection 28 that the flat surface 22 of needle holder 12 abuts against which prevents needle holder 12 from being retracted. Thus, as long as needle holder abuts against the projection 28 in each zone 13, it is "locked" in position in the front of barrel 10.

The arrangement and configuration of the zones is such that the profile 26 can be flexed away from engagement with the needle holder which frees the needle holder and allows it to be retracted into barrel 10 (or plunger 11). The particular design of projection 28 (see in particular FIG. 3) is such that the part that holds the needle holder 12 in place is relatively "abrupt", but the other end (which faces the piston 14) has an inclined or ramped surface 29. This design allows the profile 26 to be flexed away when the piston 14 is moved forwardly by abutment of the piston against the ramped surface 29 and then further forward movement of the piston.

Thus, forward movement of the piston will, at some stage, flex away the profiles 26 (with the flexing being possible due to the thin wall web portion 27 that surrounds each profile 26) and this will release needle holder 12 from engagement in front portion 15 of barrel 10.

Referring now to piston 14, in the first embodiment, piston 14 is releasably attached to plunger 11 and plunger 11 is depressurised (under vacuum). Piston 14 has a main body portion 30 which is probably best illustrated in FIG. 8. In front of main body portion is a nose portion 31, and between the nose portion 31 and main body portion 30 is an intermediate portion 32 which has the engagement means which ultimately attaches piston 14 to the needle holder 12 and this will be described in greater detail below.

Main body portion 30 supports a number of releasable locking fingers 33. These locking fingers 33 are cantilevered and extend rearwardly in the manner illustrated in FIG. 8. This allows the locking fingers 33 to be depressed or pushed inwardly towards the main body portion 30, and it is this movement that releases the piston from engagement to the front of plunger 11. Specifically, and referring to FIG. 3, the fingers 33 are naturally biased to extend proud of main body portion 30, and in doing so, abut against the front edge 34 of piston 14. However, as soon as fingers 33 are depressed, they will no longer abut against a front edge 34 of piston 14 and the vacuum within the plunger will then suck back piston 14 towards the rear of plunger 11.

The rear of the main body portion 30 of piston 14 contains a coupling 35 (see FIG. 8) to enable a seal 36 to be fitted to the rear of piston 14 (see for instance FIG. 3). The seal 36 seals the piston against the inside wall of plunger 11 such that when the piston is released, it will be sucked back towards the rear of the plunger.

The front of main body portion 30 contains a rather abrupt ring shaped shoulder portion 37 and it is this portion which strikes the ramp like surface 29 on profile 26.

In use, as plunger 11 is pushed forwardly, the attached piston 14 will move towards the locked needle holder 12, this being illustrated in FIG. 2.

Further forward movement will result in shoulder portion 37 beginning to strike the back of profile 26, this being illustrated in FIG. 3. In this position, profile 26 is just about to be flexed away from engagement with needle holder 12 but has not yet done so.

Even further forward movement of piston 14 (see FIG. 4) results in shoulder portion 37 riding underneath profile 26 and flexing profile 26 outwardly such that it no longer engages with the flat surface 22 of needle holder 12. In this position, the needle holder is released from engagement against barrel 10.

Also, the area on barrel 10 between the front portion of barrel 15 and the remainder of the barrel can be seen as a "transition zone" 38 and this is referenced in FIGS. 1 and 2. The profile of the transition zone is best illustrated in FIG. 2 and is somewhat inclined. This profile presents a striking surface to the fingers 33 on piston 14 and which hold or lock the piston to the front of plunger 11. Thus, as the piston moves forwardly from the position illustrated in FIG. 3 to the position illustrated in FIG. 4, it can also be seen that fingers 33 ride underneath the profile in the transition zone 38 and this causes the fingers to be pushed inwardly and therefore to be released from the front of plunger 11. Thus, in the position illustrated in FIG. 4, as well as needle holder 12 having been released, piston 14 has also been released.

Figure 8:
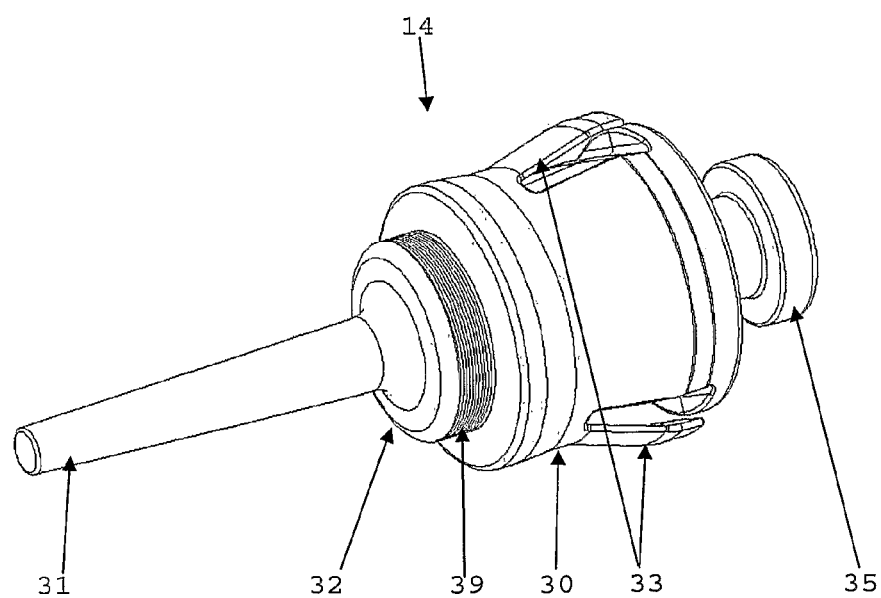
FIG. 8 illustrates the piston.

Also, the forward movement of the piston towards the needle holder causes the piston to be locked to the needle holder via the engagement means on intermediate portion 32 (see FIG. 8). In the particular embodiment, the engagement means comprise a plurality of small circumferential ribs 39 which are spaced apart and which extend about the periphery of intermediate portion 32. The "width" of this intermediate portion can be between 1-10 mm and therefore there may be provided between 2-30 or more of such circumferential ribs 39.

As piston 14 moves forwardly, the nose portion 31 on piston 14 passes into the passageway 20 which extends through needle holder 12. The shape of nose portion 31 and the slight tapering off passageway 20 is such that fluid can still flow through the passageway even when nose portion 31 is partially in the passageway as illustrated in FIG. 2.

As mentioned previously, needle holder 12 contains a larger recess 21 which communicates with passageway 20. Larger recess 21 has an internal circular wall 40 (this being referenced in FIG. 3) and wall 40 is also provided with engagement means which may be similar to the plurality of circumferential ribs 39 on the intermediate portion 32 of piston 14.

As piston 14 moves into the position illustrated in FIG. 3, the circumferential ribs 39 start to engage with the similar circumferential ribs on the wall 40. This causes the piston to be attached to the needle holder. The advantage for this particular arrangement is that the piston can be attached to the needle holder while still allowing some further forward movement without damage to the way that the piston is attached to the needle holder. Any further forward movement merely means that the circumferential ribs ride across each other to a lock together. In the position illustrated in FIG. 3, the nose portion 31 on piston 14 has also sealed passageway 20. At this stage however the needle holder has not yet been released and the piston has not yet been released.

Slight further forward movement from the position illustrated in FIG. 3 to the position illustrated in FIG. 4 will cause needle holder 12 to be released and will also cause piston 14 to be released. Importantly however, piston 14 is already attached to the needle holder by virtue of the interlocking circumferential ribs which means that when the mechanism triggers, the needle holder will already be held to the piston.

Figure 6:
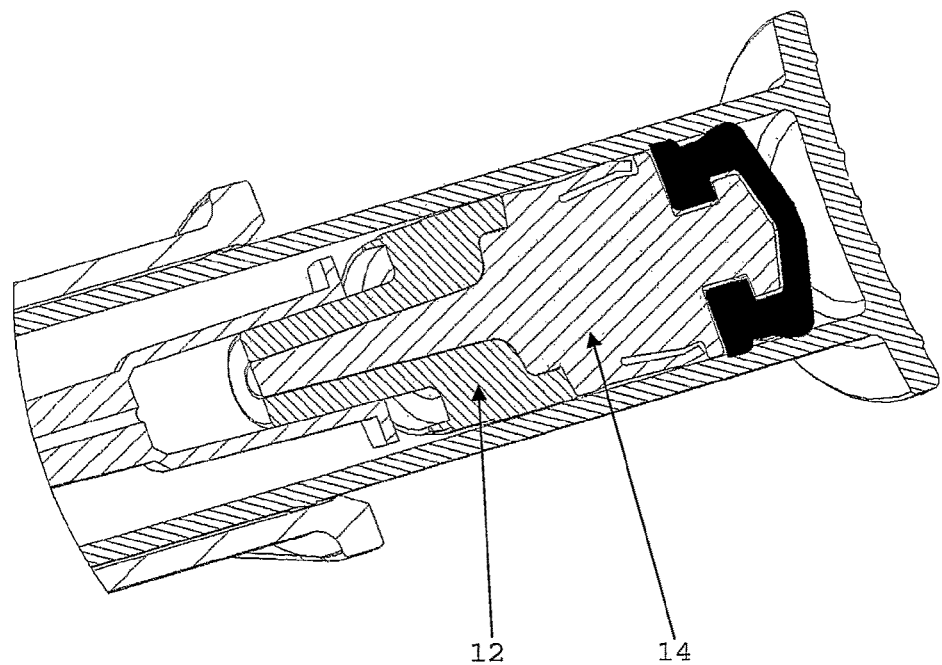
FIG. 6 illustrates the piston containing the attached needle holder in the fully retracted position.

At some stage, the piston will be released and will be sucked back into plunger 11 and will also retract the attached needle holder 12 (and needle 16) safely into the confines of the plunger. This is illustrated in FIGS. 5-6.

Second Embodiment of the Invention

The second embodiment of the invention is illustrated with reference to FIGS. 9-17.

There are many features in common with the first embodiment and therefore like references will be used for like features.

The main difference in the second embodiment of the invention is that the plunger does not contain a vacuum and the piston is not releasably attached to the front of the plunger. Instead, when the piston is attached to the needle holder, the plunger has to be retracted manually to pull the piston, the needle holder and the contaminated needle into the safety of the barrel body.

Because it might be possible to push the plunger back again to re-expose the needle, the second embodiment of the invention also has a mechanism that locks the piston into the back of the syringe body and allows the plunger to be snapped away thereby making it virtually impossible to push the piston back to the front of the syringe body to re-expose the needle.

Because there is no need to have a releasable piston, there is also no need to have a particular "transition zone" 38 as there are no fingers on the piston to be depressed to release the piston from the plunger. Therefore, the syringe (see FIG. 9) can have a more conventional shape.

The syringe in the "manual" embodiment of the invention has a needle holder 12 which is identical to the needle holder of the first embodiment and is again held in place by zones 13 on the front portion 15 of barrel 10. Thus, this part of the invention is identical to the previous embodiment.

The plunger comprises a plunger stem 42 and a plunger head, which in the particular embodiment is again called a piston 43. Piston 43 again has a nose portion 44 and an intermediate portion 45 which is identical to the intermediate portion of the previous embodiment and therefore again contains the circumferential ribs 39.

Needle holder 12 again contains the recess 21 with the wall 40 containing the circumferential ribs as well and the attachment of piston 43 in this embodiment to needle holder 12 is the same as described in the first embodiment and again has the advantage of providing some adjustability in the range of attachment positions.

The front of piston 43 contains the abutment shoulder 46 which strikes against the profile on the zone 13 and flexes the zone away in a manner similar to that described with the first embodiment.

Thus, FIG. 10 shows piston 43 moving towards needle holder 12 but needle holder 12 is still held in place by the profiles 26 on zones 13.

In FIG. 11, shoulder 46 has ridden underneath profile 26 and has flexed the profile away from engagement with needle holder 12, so needle holder 12 is now in the released position. At the same time, nose portion 44 has entered into the passageway 20 of needle holder 12 and the ribs on the piston and on the needle holder have engaged to lock the two components together.

The plunger can now be retracted (see FIG. 13) to pull back the piston 43 and the attached needle holder 12 towards the rear of barrel 10.

FIG. 14 shows the piston 43 and the attached needle holder 12 at the rearmost portion of barrel 10.

In the second embodiment, the rearmost portion of barrel 10 contains a number of locking lugs 47 (in the particular embodiment four locking lugs 47 are provided and are probably best illustrated in FIG. 16). These locking lugs comprise inwardly extending projections (see FIG. 14).

Piston 43 has a rearmost T-shaped head portion 48 having a ramped side wall 49 and this means that as the plunger is retracted, side wall 49 will strike against a respective locking lug 47 and will push the lug out of the way.

Referring to FIG. 15, head portion 48 has now been retracted to its furthermost extent and the locking lugs 47 are now positioned behind head portion 48.

Thus, piston 43 is now locked in the retracted position and cannot be pushed forwardly to try to re-expose the contaminated needle from the front of the syringe.

As a further safety measure, the plunger 11 has a necked portion immediately behind head portion 48 which allows the plunger to be snapped away in the manner illustrated in FIG. 17 to make it even more difficult (if not impossible) to push the piston 43 back a long barrel 10 to re-expose needle 16.

Third Embodiment of the Invention

The third embodiment of the invention is illustrated with reference to FIGS. 18-21.

This embodiment is similar to the first embodiment in that there is provided a releasable piston 50 in the front of plunger 51. The attachment of piston 50 to the needle holder 52 is as described in the previous embodiments.

The main difference is that the vacuum in plunger 51 can be made "on demand" and typically just prior to use. This is done by having a slideable end wall 53 in plunger 51 which is sealingly but still slidingly engaged to the inside wall of plunger 51. End wall 53 is attached to a retraction member 54 which enables the end wall to be pulled back from the position illustrated in FIG. 19 to the position illustrated in FIG. 20 to cause a vacuum to be created in plunger 51 just prior to use.

When end wall 53 moves to the fully retracted position (see FIG. 20), a portion of the end wall can expand to release the retraction member 54 such that the retraction member 54 can be removed and will not be in the way.

Figure 21:
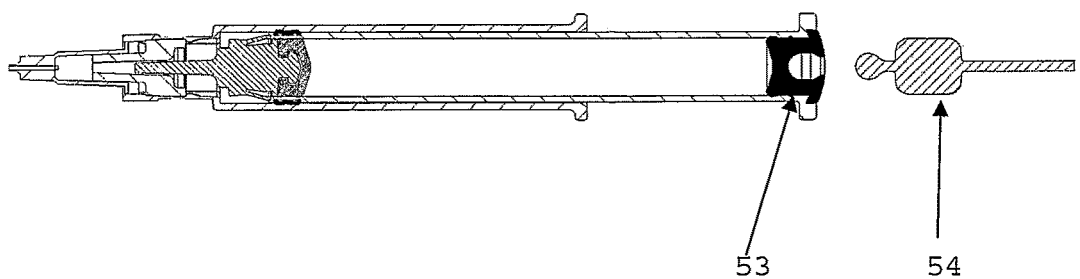

In the position illustrated in FIG. 21, the syringe can be now used in the manner similar to that described with reference to the first embodiment as vacuum has now been created in plunger 51.

Fourth Embodiment of the Invention

The fourth embodiment of the invention is illustrated with reference to FIGS. 22-28. In this particular embodiment, the needle holder is securely but releasably held in the front of the barrel using deflectable clips which are cantilevered, and because holes are now created in the side wall of the barrel, the design of the needle holder is somewhat different, as is the design of the piston and possibly some other parts.

Figure 22:
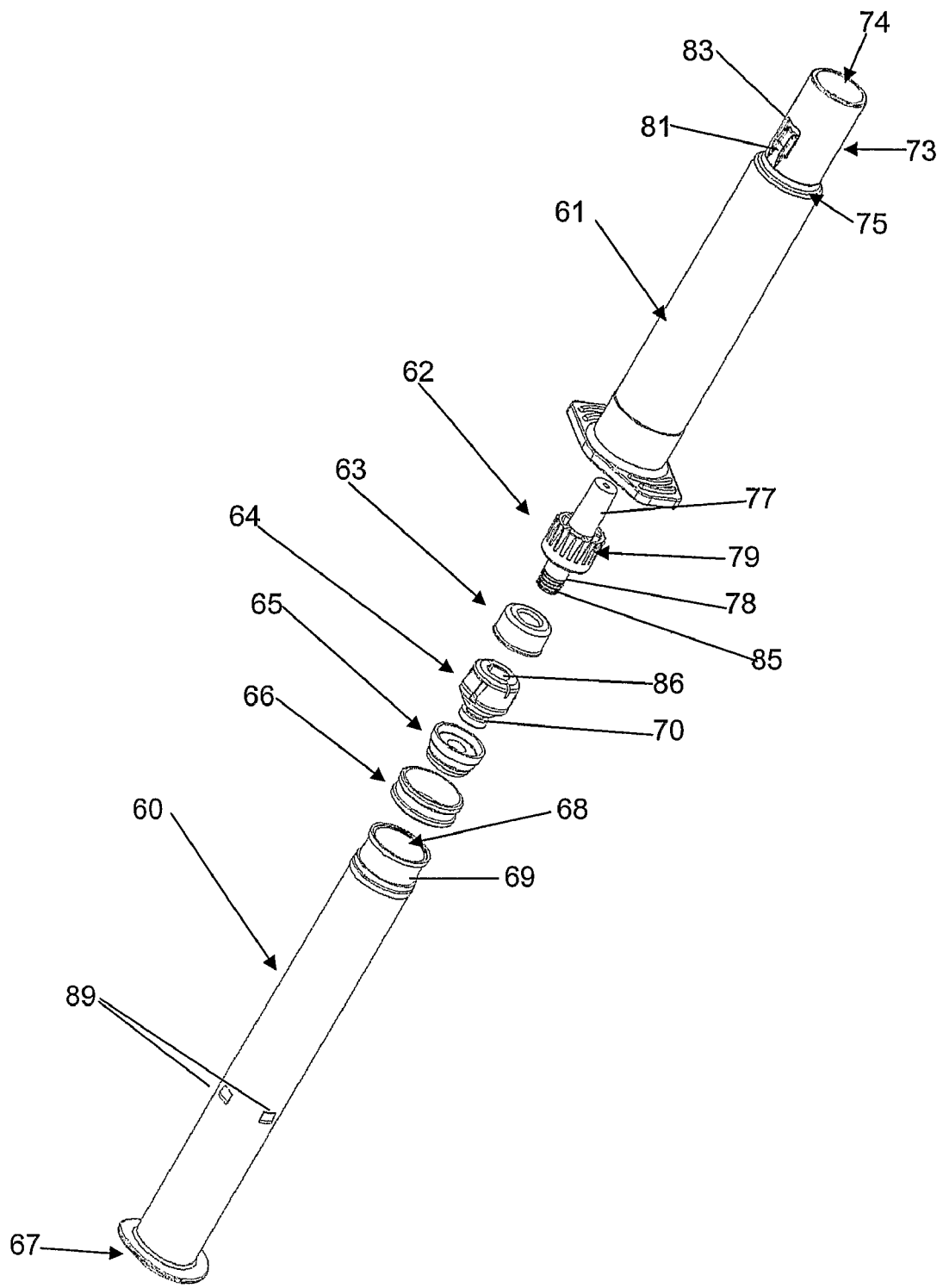

Referring initially to FIG. 22, there is illustrated the main parts of the device which include a plunger 60, a barrel 61, a needle holder (luer) 62, a needle holder seal 63 which extends about the rear of the needle holder, a piston 64 which is releasably attached to the otherwise open front of plunger 60, a vacuum seal 65 which is attached to the rear of piston 64, and a plunger seal 66 which extends about the outside of the front of plunger 60. These parts will now be described in greater detail.

Plunger 60 is substantially hollow and has a closed rear end 67 and an open front end 68. Open front end 68 has a necked portion 69 immediately behind it and the necked portion 69 functions to accommodate the plunger seal 66. Plunger 60 is provided with small clips 89 more towards the rear of the plunger and the function of these will be described in greater detail below.

The open front end 68 of plunger 60 is sealed by a two-part member comprising piston 64 and piston seal 65. Piston 64 has a rear necked projection 70 (see for instance FIG. 24) and seal 65 can fit to the rear of piston 64 by being pushed into engagement about necked projection 70. The function of seal 65 is to sealingly engage against the inside wall of the front of piston 60 to provide a vacuum seal and thereby to prevent loss of vacuum within plunger 60.

Figure 24:
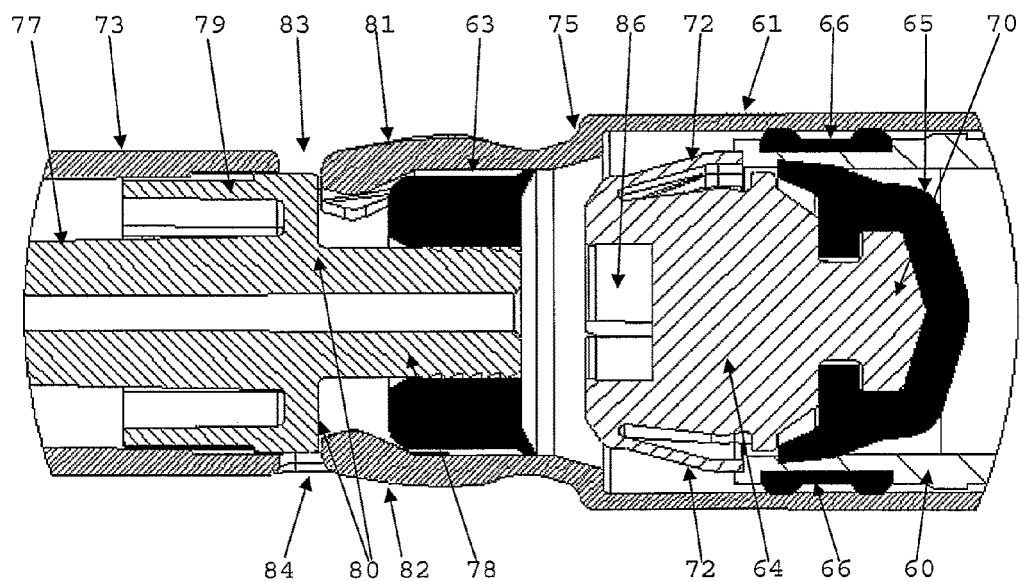
Figure 25:
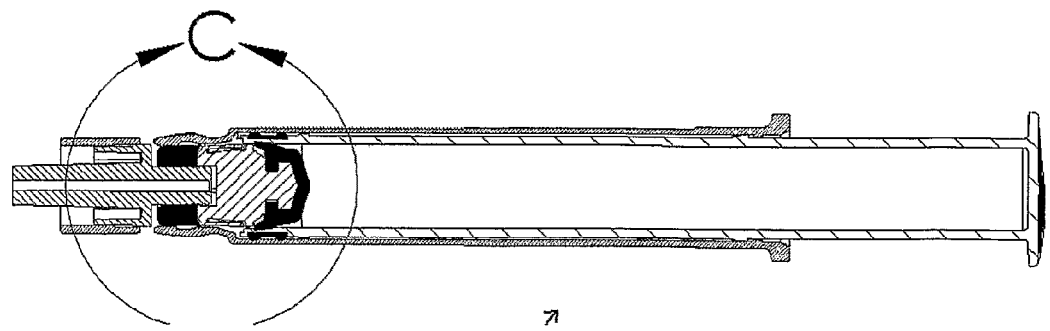

Piston 64 is releasably engaged to the front of plunger 60. To achieve this, piston 64 contains a number of deflectable clips or finger members 72. These are best illustrated in FIG. 24. Clips 72 are somewhat cantilevered rearwardly from the front of the piston and the free ends of clip 72 engage against the front edge of plunger 60 (see for instance FIG. 24). In this engaging position, piston 64 is sealingly engaged to the front of plunger 60 and cannot be released and therefore cannot be retracted (sucked back) into plunger 60 by virtue of the vacuum within the plunger. However, if clips 72 are pushed inwardly, they will be released from the front edge of plunger 60 and then the piston can be sucked back into the interior of plunger 60. Clips 72 can be pushed inwardly to the "release" position as the plunger is pushed towards the front of the barrel and this will be explained in the next paragraph.

Barrel 61 contains a front nose portion 73 which has an open front end 74. The nose portion 73 is of reduced diameter relative to the remainder of barrel 61 and therefore a shoulder portion 75 is provided (see for instance FIG. 22 and FIG. 24). This shoulder portion assists in the deflection of clips 72 from the locked position to the release position.

Thus, as plunger 60 moves forwardly to the front of barrel 61, the position of piston 64 is as illustrated in FIG. 24 which is where piston 64 is almost in engagement with shoulder portion 75. At this stage, clips 72 on piston 64 are in the locking position to lock the piston against the front of the plunger. However, further forward movement of plunger 60 from the position illustrated in FIG. 24 to the position illustrated in FIG. 26 results in clips 72 striking shoulder portion 75 and riding underneath shoulder portion 75 and this causes clips 72 to be deflected inwardly to the position where the clips no longer engage against the edge of plunger 60. At this point, piston 64 is released from engagement against the front of plunger 60.

However, just prior to the piston becoming released from plunger 60, the needle holder (luer) 62 is released. Needle holder 62 comprises a front nose portion 77 (see FIG. 22 and FIG. 24), a rear stem portion 78, and an intermediate side portion 79. A passageway extends through the needle holder 62 into which a steel needle (not illustrated) can be fitted and to allow passage of medicine or other liquid from the syringe barrel and through the needle.

The side wall 79 of the needle holder 62 engages against the inside wall of nose portion 73 and the side wall 79 contains a small shoulder as does the inside wall of nose portion 73, the function being to prevent needle holder 62 from being pushed out the otherwise open front 74 of barrel 61.

As well, the side wall 79 extends outwardly from stem portion 78 to create a rather large annular abutment or shoulder 80.

The nose portion 73 of barrel 65 contains a pair of diametrically opposite openings 83, 84 which are roughly rectangle. A clip 81, 82 extends in a cantilevered manner across each opening. Each clip 81, 82 is attached to barrel 61 at a rear portion and the free end of each clip 81, 82 is directed to a front of the barrel. The clips can be formed integrally with the remainder of the nose portion and because the clips are cantilevered, the clips have a degree of spring. Each clip is configured such that it naturally adopts a locking position where the free end of the clip abuts against shoulder 80 on needle holder 62 as illustrated in FIG. 24. Thus, needle holder 62 is securely held in position in the nose portion 73 of barrel 61 by the clips 81, 82.

As openings 83, 84 extend through the side wall of barrel 61, a seal is required to prevent a medicine leaking through these openings. In the particular embodiment, there is provided a seal 63 which is fitted about the stem portion 78 of needle holder 62, this being best illustrated in FIG. 24. Seal 63 prevents medicine from leaking between the needle holder and the barrel and through openings 83, 84. Seal 63 comprises a cylindrical member formed with a central opening to allow it to be fitted about stem portion 78. The fitting of seal 63 about stem portion 78 is such that this seal can be pushed forwardly along stem portion 78 when piston 64 is moved forwardly sufficiently to abut against the rear of seal 63, together with further forward movement of the plunger.

Seal 63 is positioned below clips 81, 82 (see FIG. 24) and it can be seen that clips 81, 82 are curved slightly inwardly. Consequently, when seal 63 is pushed forwardly along stem portion 78 (by forward pushing of the plunger), the seal will ride underneath the clips 81, 82 and because of the inwardly curved configuration of the clips, this seal will cause to clips to be pushed outwardly by a few millimeters but this is sufficient to release the clips from engagement against the underside of shoulder 80 on the needle holder. Thus, as soon as this occurs, the needle holder 62 is no longer locked into the nose portion of the barrel.

Stem portion 78 of needle holder 62 contains a series of spaced ribs 85 which are similar to that described in earlier embodiments and which form part of a variable locking arrangement. Initially, seal 63 seats about the spaced ribs 85 (see FIG. 24), but as this seal is pushed forwardly (see FIG. 26), the ribs become exposed. The front of piston 64 contains a recess 86 (see for instance FIG. 22 and FIG. 24). The inside wall of the recess also contains a series of spaced ribs in a manner not dissimilar to that described in previous embodiments.

Therefore, as the plunger is pushed towards the end of barrel 61 and consequently piston 64 approaches the rear of needle holder 62, the front face of piston 64 abuts against and begins to push forwardly the seal 63 which exposes the ribs 85 on stem portion 78 and at the same time, the stem portion 78 moves into recess 86 in the front of piston 64 and, as recess 86 also contains ribs, the ribs engage to lock the needle holder to piston 64.

Figure 27:
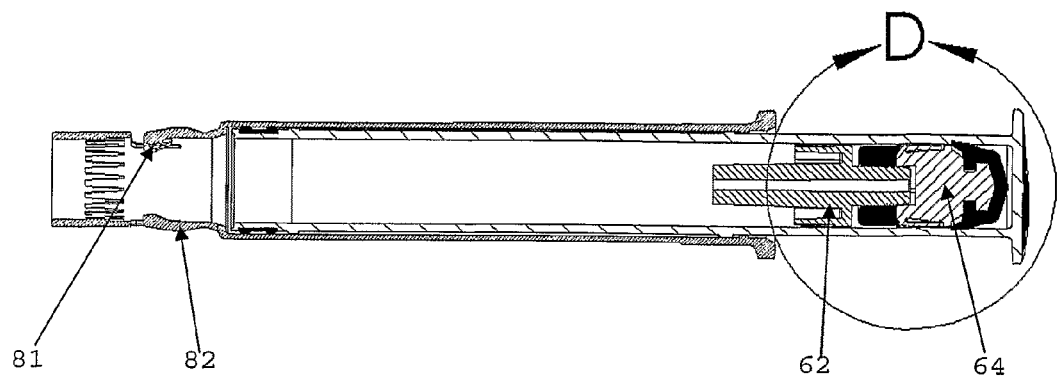
Figure 28:
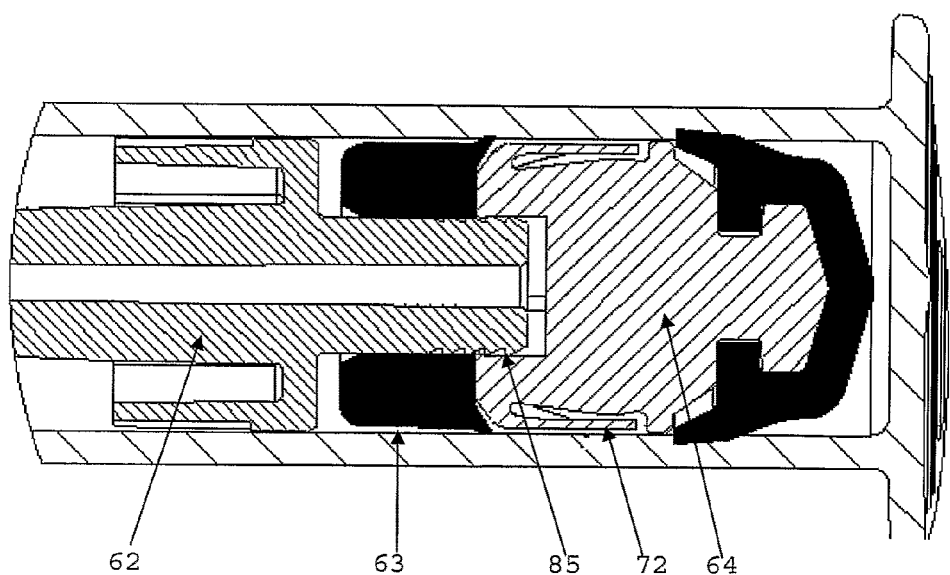

The construction of the various components is such that clips 81, 82 deflect outwardly to release needle holder 62 at about the same time that needle holder 62 locks to piston 64 and the final step is inward deflection of clips 72 to release piston 64 from the front of the plunger 60 which causes the piston 64 and the attached needle holder to be sucked back into the rear of the plunger. This final position is illustrated in FIGS. 27-28.

Figure 23:
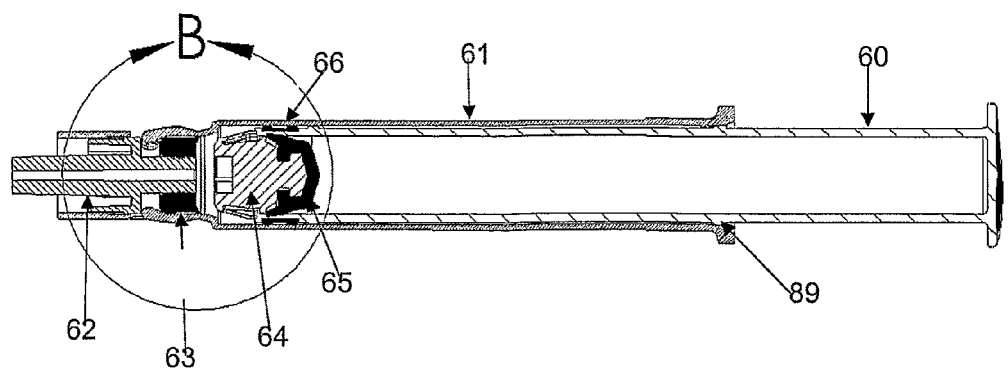

Plunger 60 contains a number of small projecting clip members 89 (see for instance FIG. 22). These clip members contact the rear portion of barrel 61 to provide some resistance in further forward movement of plunger 60. Thus, and as illustrated in FIG. 23, plunger 60 can be fitted into the open end of barrel 61 and easily and smoothly pushed forwardly until clip members 89 engage against the rear of barrel 61. It is still possible to push the plunger further forward (thereby triggering the retraction mechanism), but to do so it is necessary to apply a slightly larger amount of force to push the clip members 89 past the end of barrel 61. This arrangement prevents plunger 60 from inadvertently moving forward to the triggering position, and enables the entire assembly to be packaged in the position illustrated in FIG. 23 with reduced possibility of handling of the packaged device inadvertently causing further forward movement of the plunger and therefore an inadvertent triggering of the retraction mechanism.

Fifth Embodiment of the Invention

FIGS. 29-35 illustrates a fifth embodiment of the invention.

Figure 29:
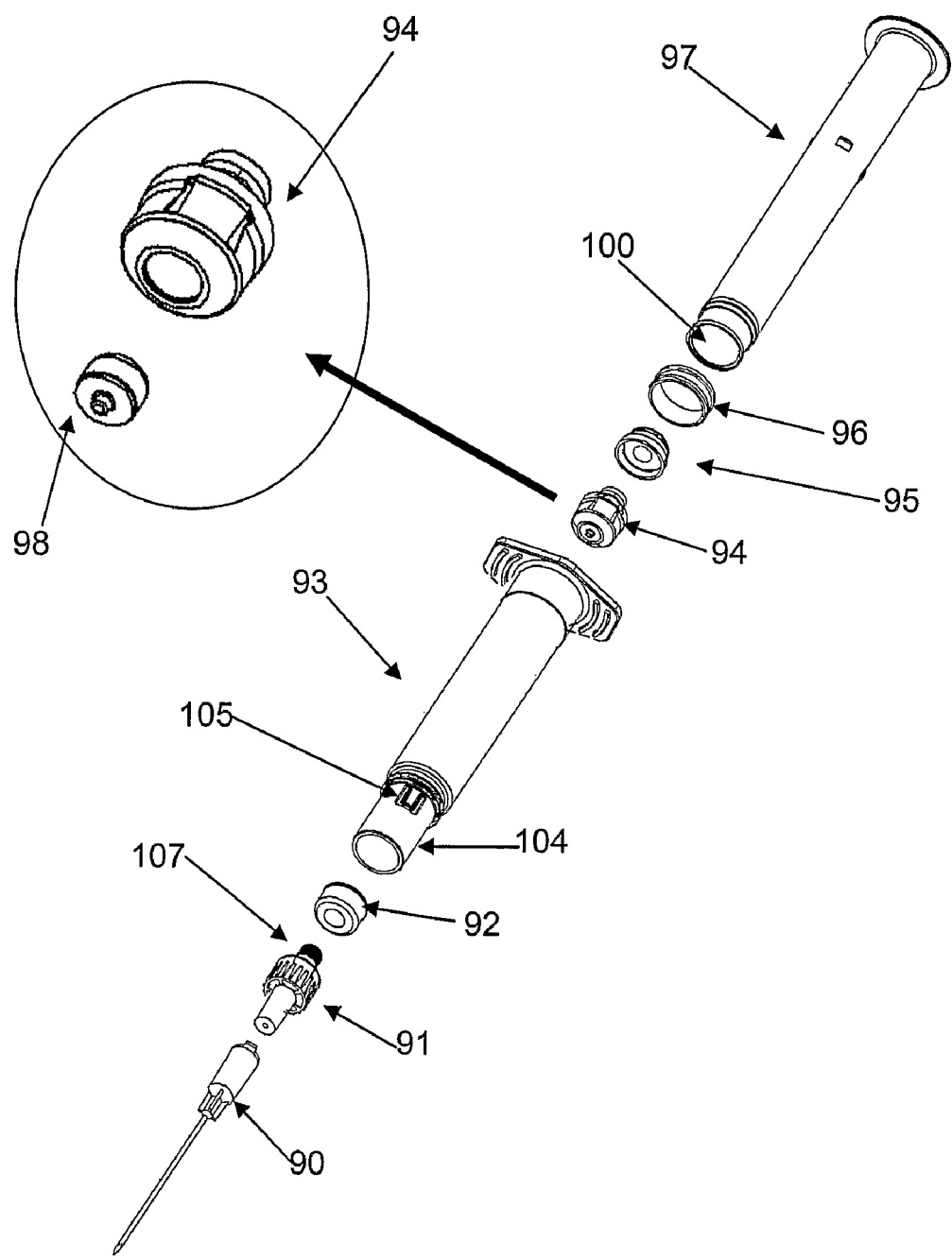

Referring initially to FIG. 29, there is illustrated an exploded view which comprises a luer needle 90, a luer (needle holder) 91, a luer seal 92, an outer barrel 93, a small piston 94, a vacuum seal 95, a plunger seal 96, and a plunger 97. Plunger 97 has an open front end 100.

FIG. 31 illustrates most of these components assembled. In FIG. 31, there is more clearly illustrated that the open front end 100 of the plunger 97 is closed by being plugged with piston 94. The rear end of piston 94 contains the vacuum seal 95 and vacuum seal 95 functions to maintain the vacuum in plunger 97. The outer wall of plunger 97 is fitted with the plunger seal 96 to prevent any liquid in the syringe passing between the outer wall of the plunger and the inner wall of barrel 93.

Piston 94 (illustrated least in FIG. 31) comprises a number of deflectable locking fingers 101 which lock against the front wall of plunger 97. Deflectable locking fingers 101 prevent the piston 94 from being sucked back into plunger 97 because of the vacuum within plunger 97.

Piston 94 contains a forward recess or cavity 102 in which is fitted a piston plug 98. Plug 98 sits in a front part of cavity 102 but can be pushed further into the cavity (this will be described in greater detail with reference to FIG. 33). The piston plug 98 contains a small forwardly extending nose portion 103.

Figure 26:
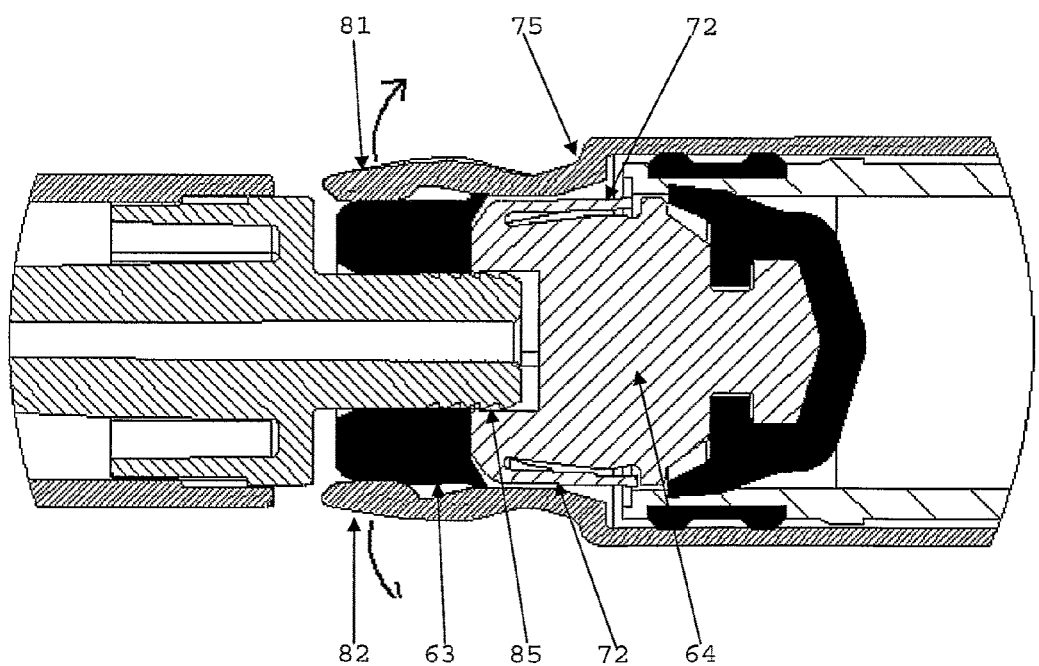

The front of barrel 93 contains a step down portion 104 (see FIG. 29) which contains a pair of deflectable clips 105 which are similar to that described with reference to the earlier embodiments (FIG. 24 and FIG. 26 for instance).

Luer 91 (see FIG. 31) contains a through passageway 106 which communicates with needle 90. The inner end of luer 91 is fitted with the luer seal 92 as illustrated in FIG. 31. Luer seal 92 prevents liquid in the barrel from passing through the opening around each clip 105. Luer seal 92 is fitted over a cylindrical portion 107 (see also FIG. 29) of luer 91. The cylindrical portion 107 contains a plurality of circumferential ribs or teeth etc 108 (see FIG. 33 at least).

In use, liquid within barrel 93 can be pushed through needle 90 by advancement of plunger 97 and at the point illustrated in FIG. 31, the front of plunger 97 (that is piston 94) is almost touching the rear of luer 91. In this position, almost all the liquid within the barrel has been pushed through or into needle 90.

Further slight advancement of plunger 97 causes the small nose portion 103 on the front of piston plug 98 to plug the open rear passageway 106 to prevent further positive flow and backflow of liquid. This ensures that the same dose is given whether activation of the needle retraction mechanism occurs while the needle is still inserted in the patient or whether the needle is withdrawn prior to activating the retraction mechanism. It also helps prevents blood splatter during retraction as it retains any blood in the needle because there is no further positive flow.

At the same time, the locking fingers 101 on the piston (and that prevent the piston from being sucked back into plunger 97), abut against a shoulder 109 on barrel 93 this being best illustrated in FIG. 32. At this stage however the piston is still locked to the front of plunger 97.

Figure 33:
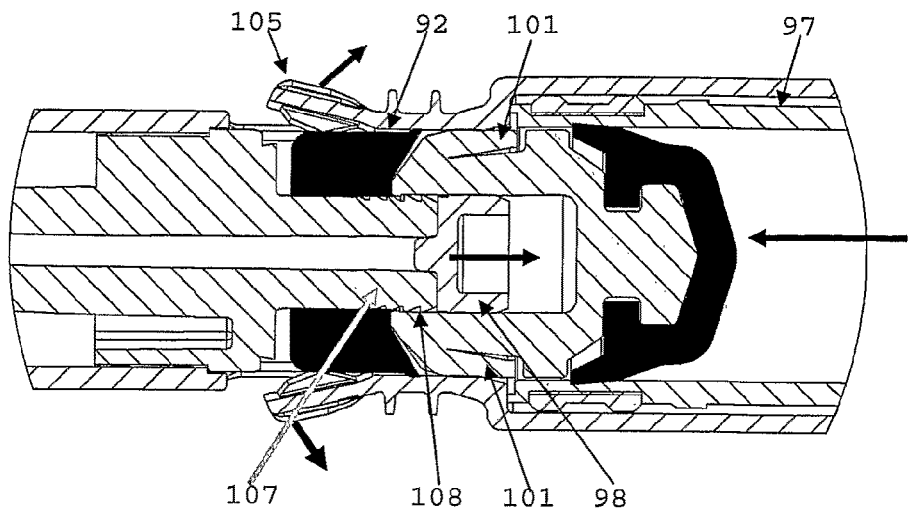
Figure 34:
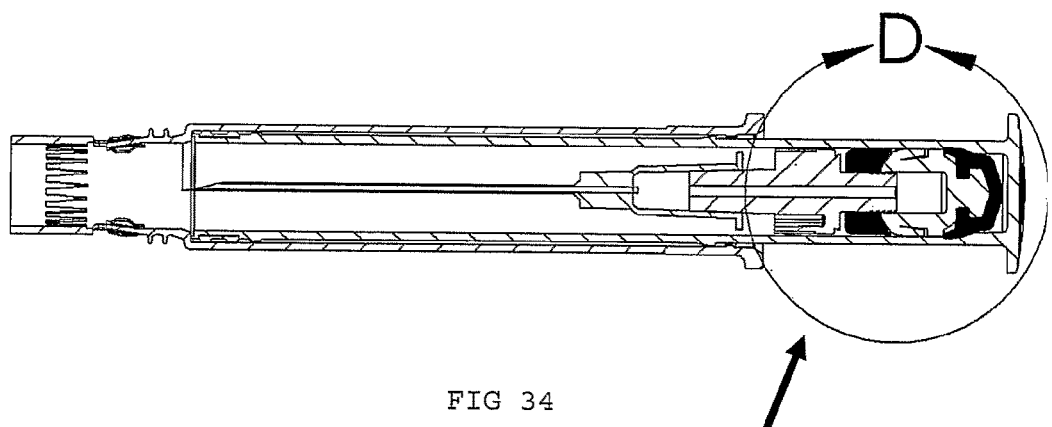

Further slight advancement of plunger 97 causes the components to adopt a position illustrated in FIG. 33. In FIG. 33, the plunger 97 has been pushed forwardly by a few more millimeters. As this occurs, the locking fingers 101 pass underneath the shoulder 109 and at some point the locking fingers 101 will become released from engagement with the front of plunger 97.

As well, the front of piston 94 has begun to push the luer seal 92 along the cylindrical portion 107 causing the circumferential ribs or teeth 108 to become exposed. Cylindrical portion 107 pushes the small piston plug 98 back into cavity 102 by a few millimeters but at all times, the small nose portion 103 on piston plug 98 continues to seal the passageway 106. Part of cylindrical portion 107 therefore passes into the cavity 102 and the ribs/teeth 108 engage against the inside wall of the cavity 102 which may also contain teeth/ribs etc. This causes the luer 91 (needle holder) to become attached to piston 94. The locking fingers 101 have become released from the front of plunger 97. Pushing the luer seal 92 forwardly along the cylindrical portion 107 causes the luer seal to deflect clips 105 to the release position illustrated in FIG. 33 where the luer 91 is no longer locked against the clips.

Figure 35:
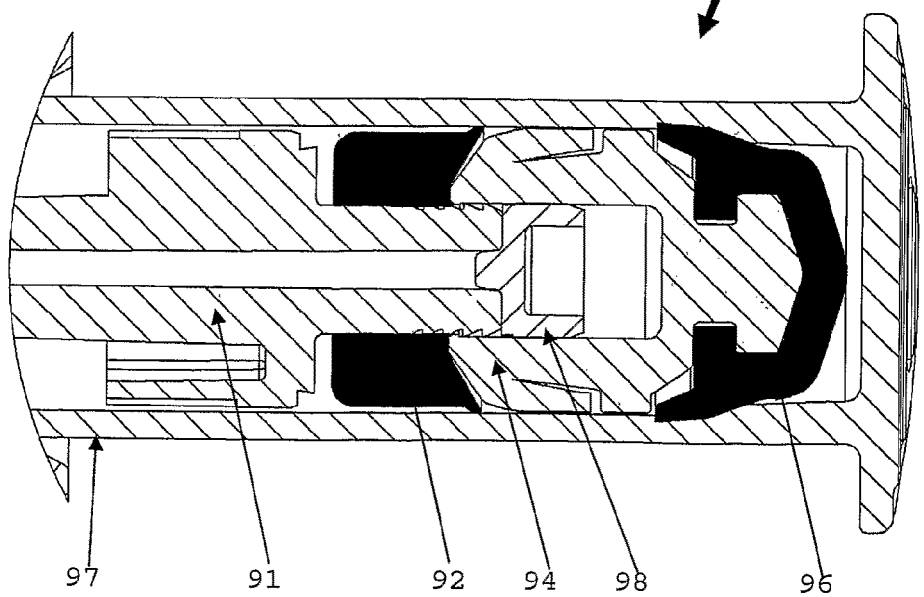

The arrangement therefore (a) causes luer 91 to be variably locked to piston 94 and (b) causes piston 94 to become released from the front of plunger 97 and (c) causes luer 91 to become released from the front of barrel 93 which then enables these components to be retracted into plunger 97 under the influence of vacuum within the plunger. The retracted position is illustrated in FIG. 35.

Throughout the specification and the claims (if present), unless the context requires otherwise, the term "comprise", or variations such as "comprises" or "comprising", will be understood to apply the inclusion of the stated integer or group of integers but not the exclusion of any other integer or group of integers.

Throughout the specification and claims (if present), unless the context requires otherwise, the term "substantially" or "about" will be understood to not be limited to the value for the range qualified by the terms.

It should be appreciated that various other changes and modifications can be made to any embodiment described without departing from the spirit and scope of the invention.

The invention claimed is:

1. A medical syringe comprising
a barrel having a front end and a open rear end,
a plunger which is slidable in the barrel, the plunger being under reduced pressure and having an open front which is plugged by a piston, the piston being releasably locked to the front of the plunger,
a luer which is in the front end of the barrel and is releasably locked against retraction by a locking means, the luer having a through passageway to allow liquid to be expelled from the syringe, the luer containing a rear portion which is formed with a plurality of circumferential locking ribs, the piston containing a cavity,
whereby advancement of the plunger along the barrel causes the rear portion of the luer to enter into the cavity and enables the luer to be locked to the piston by engagement of one or more of the locking ribs with an internal wall of cavity, and
wherein the plunger remains stationary relative to the barrel during retraction of the piston once the piston has been unlocked from the front of the plunger.

2. The syringe as claimed in claim 1, wherein cavity contains a piston plug which is pushed into the cavity upon contact of the piston plug with the rear portion of the luer.

3. The syringe as claimed in claim 2, wherein the piston plug contains a forward nose portion which seals the through passageway when the piston plug is pushed against the rear portion of the luer.

4. The syringe as claimed in claim 1, wherein the piston contains at least one deflectable locking finger which locks the piston to the front of the plunger, whereby advancement of the plunger at some stage causes the at least one deflectable locking finger to be deflected to a release position where the piston is no longer locked to the front of plunger.

5. The syringe as claimed in claim 1, wherein the locking means comprises at least one clip on barrel and which can move between a luer locking position and a luer unlocking position.

6. The syringe as claimed in claim 5, wherein the luer is fitted with a luer seal, the luer seal extending about the rear portion of the luer and adapted to be pushed forwardly along the rear portion to expose locking ribs, movement of luer seal also causing the at least one clip to move to the unlocking position to release luer from engagement to barrel.

7. The syringe as claimed in claim 1, wherein the cavity comprises a bore that extends axially into the piston from a front wall thereof.

8. A needle containing medical device having a retractable needle, the device comprising:
- an outer body having a front portion through which the needle can extend, and a rear portion,
- an inner member which can slide within the outer body,
- a releasable needle holder in a front portion of the outer body, a needle attached to the needle holder,
- wherein the front portion of the outer body contains at least one side opening extending therethrough, a clip having one part attached relative to the outer body, and extending in a cantilevered manner at least partially along the side opening, the clip naturally being in a needle holding position but able to be deflected to a needle release position,
- wherein the inner member is able to move within the outer body to the front portion of the outer body and wherein the inner member is able to deflect the at least one clip to the release position thereby enabling the needle holder to be retracted, and
- wherein the inner member remains stationary relative to the outer body during retraction of the needle holder.

9. The device as claimed in claim 8 wherein the inner member is provided with a series of spaced needle holder engaging means, and the needle holder is provided with a series of spaced inner member engaging means thereby enabling the inner member to be attached to the needle holder at least one of the series of engaging means.

10. A needle containing medical device according to claim 8, wherein the clip is formed integrally with the outer body.

11. A needle containing medical device according to claim 8, wherein the releasable needle holder abuts the clip to deflect the clip from the needle holding position to the needle release position.

12. A needle containing medical device according to claim 8, wherein the inner body is under reduced pressure.

* * * * *